United States Patent
Di Paolo et al.

(10) Patent No.: US 10,080,756 B2
(45) Date of Patent: Sep. 25, 2018

(54) COMBINATION METHODS FOR TREATING CANCERS

(71) Applicant: Gilead Sciences, Inc., Foster City, CA (US)

(72) Inventors: Julie Di Paolo, San Francisco, CA (US); Astrid Clarke, Bainbridge Island, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/622,737

(22) Filed: Jun. 14, 2017

(65) Prior Publication Data

US 2018/0008608 A1 Jan. 11, 2018

Related U.S. Application Data

(63) Continuation of application No. 14/796,795, filed on Jul. 10, 2015, now Pat. No. 9,707,236.

(Continued)

(51) Int. Cl.
*A61K 31/5377* (2006.01)
*A61K 31/475* (2006.01)
(Continued)

(52) U.S. Cl.
CPC ........ *A61K 31/5377* (2013.01); *A61K 31/475* (2013.01); *A61K 31/4985* (2013.01); *A61K 45/06* (2013.01)

(58) Field of Classification Search
CPC .................. A61K 31/5377; C07D 265/30
(Continued)

(56) References Cited

U.S. PATENT DOCUMENTS

| 5,593,997 A | 1/1997 | Dow et al. |
| 5,658,857 A | 8/1997 | Andree et al. |

(Continued)

FOREIGN PATENT DOCUMENTS

| CA | 2175837 A1 | 5/1995 |
| DE | 4337609 A1 | 5/1995 |

(Continued)

OTHER PUBLICATIONS

Krisenko, "Calling in SYK: SYK's dual role as a tumor promoter and tumor suppressor in cancer," Biochimica et Biophysica Acta 1853 (2015), pp. 254-263.*

(Continued)

*Primary Examiner* — Craig D Ricci
*Assistant Examiner* — Janet L. Coppins
(74) *Attorney, Agent, or Firm* — Sheppard Mullin Richter & Hampton LLP

(57) ABSTRACT

Disclosed are methods for treating a cancer in a subject (e.g., a human) in need thereof, comprising administering to the subject a therapeutically effective amount of a compound of formula I:

(Continued)

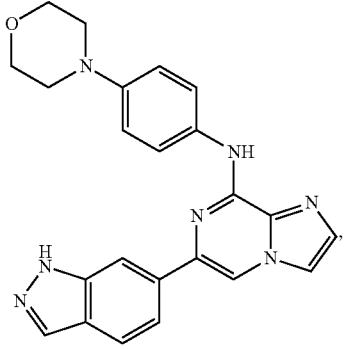

(I)

or a pharmaceutically acceptable salt thereof, in combination with a vinca-alkaloid, or a pharmaceutically acceptable salt thereof. The subject may be very high risk or high risk for the cancer and may not respond to either agent administered as a sole therapy. The subject who has the cancer may also be refractory to at least one chemotherapy treatment, or is in relapse after treatment with chemotherapy, or both. The cancer may be a hematologic malignancy, such as leukemia or lymphoma, or a solid tumor cancer, such as pancreatic, lung and colon cancer.

34 Claims, 26 Drawing Sheets

Related U.S. Application Data

(60) Provisional application No. 62/024,424, filed on Jul. 14, 2014.

(51) Int. Cl.
  *A61K 45/06*  (2006.01)
  *A61K 31/4985*  (2006.01)

(58) Field of Classification Search
  USPC ....................................... 544/120; 514/233.2
  See application file for complete search history.

(56) References Cited

U.S. PATENT DOCUMENTS

| | | | |
|---|---|---|---|
| 5,783,576 A | 7/1998 | Roos et al. |
| 5,846,514 A | 12/1998 | Foster et al. |
| 6,334,997 B1 | 1/2002 | Foster et al. |
| 6,919,340 B2 | 7/2005 | Currie et al. |
| 6,919,341 B2 | 7/2005 | Paruch et al. |
| 7,160,885 B2 | 1/2007 | Currie et al. |
| 7,189,723 B2 | 3/2007 | Mitchell et al. |
| 7,259,164 B2 | 8/2007 | Mitchell et al. |
| 7,312,341 B2 | 12/2007 | DeSimone et al. |
| 7,405,295 B2 | 7/2008 | Currie et al. |
| 8,440,667 B2 | 5/2013 | Mitchell et al. |
| 8,450,321 B2 | 5/2013 | Mitchell et al. |
| 8,455,493 B2 | 6/2013 | Mitchell et al. |
| 8,697,699 B2 | 4/2014 | Mitchell et al. |
| 8,748,607 B2 | 6/2014 | Mitchell et al. |
| 8,765,761 B2 | 7/2014 | Mitchell et al. |
| 8,796,270 B2 | 8/2014 | Mitchell |
| 8,962,835 B2 | 2/2015 | Mitchell et al. |
| 9,120,811 B2 | 9/2015 | Mitchell et al. |
| 9,212,191 B2 | 12/2015 | Mitchell et al. |
| 9,290,505 B2 | 3/2016 | Blomgren et al. |
| 9,376,441 B2 | 6/2016 | Currie et al. |
| 9,382,256 B2 | 7/2016 | Casteel et al. |
| 9,504,684 B2 | 11/2016 | Blomgren et al. |
| 9,562,056 B2 | 2/2017 | Blomgren et al. |
| 9,567,348 B2 | 2/2017 | Mitchell et al. |
| 9,657,023 B2 | 5/2017 | Elford et al. |
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 2003/0212073 A1 | 11/2003 | Currie et al. |
| 2004/0063715 A1 | 4/2004 | Paruch et al. |
| 2004/0067951 A1 | 4/2004 | DeSimone et al. |
| 2004/0072835 A1 | 4/2004 | Paruch et al. |
| 2004/0102455 A1 | 5/2004 | Burns et al. |
| 2004/0220189 A1 | 11/2004 | Sun et al. |
| 2005/0009832 A1 | 1/2005 | Sun et al. |
| 2005/0054648 A1 | 3/2005 | Mitchell et al. |
| 2005/0054649 A1 | 3/2005 | Currie et al. |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0288295 A1 | 12/2005 | Currie et al. |
| 2006/0069084 A1 | 3/2006 | Burns et al. |
| 2006/0084650 A1 | 4/2006 | Dong et al. |
| 2006/0183746 A1 | 8/2006 | Currie et al. |
| 2007/0027135 A1 | 2/2007 | Bruncko et al. |
| 2007/0072860 A1 | 3/2007 | Bruncko et al. |
| 2007/0117804 A1 | 5/2007 | Zhao et al. |
| 2009/0221612 A1 | 9/2009 | Mitchell et al. |
| 2010/0152159 A1 | 6/2010 | Mitchell et al. |
| 2010/0222323 A1 | 9/2010 | Mitchell et al. |
| 2010/0305122 A1 | 12/2010 | Bruncko et al. |
| 2010/0305125 A1 | 12/2010 | Borchardt et al. |
| 2012/0157470 A1 | 6/2012 | Catron et al. |
| 2012/0220582 A1 | 8/2012 | Mitchell et al. |
| 2013/0023499 A1 | 1/2013 | Mitchell et al. |
| 2013/0210802 A1 | 8/2013 | Blomgren et al. |
| 2013/0231330 A1 | 9/2013 | Mitchell et al. |
| 2013/0237520 A1 | 9/2013 | Mitchell et al. |
| 2013/0237521 A1 | 9/2013 | Mitchell et al. |
| 2013/0267496 A1 | 10/2013 | Mitchell et al. |
| 2013/0310363 A1 | 11/2013 | Mitchell et al. |
| 2013/0338142 A1 | 12/2013 | Blomgren et al. |
| 2014/0148430 A1 | 5/2014 | Blomgren et al. |
| 2014/0336169 A1 | 11/2014 | Mitchell et al. |
| 2014/0357627 A1 | 12/2014 | Mitchell et al. |
| 2015/0038488 A1 | 2/2015 | Currie et al. |
| 2015/0038504 A1 | 2/2015 | Casteel et al. |
| 2015/0038505 A1 | 2/2015 | Elford et al. |
| 2015/0150881 A1 | 6/2015 | Di Paolo et al. |
| 2015/0175616 A1 | 6/2015 | Blomgren et al. |
| 2015/0266902 A1 | 9/2015 | Blomgren et al. |
| 2016/0031894 A1 | 2/2016 | Mitchell et al. |
| 2016/0058758 A1 | 3/2016 | Blomgren et al. |
| 2016/0166579 A1 | 6/2016 | Di Paolo et al. |
| 2016/0166580 A1 | 6/2016 | Casteel et al. |
| 2016/0168155 A1 | 6/2016 | Fung et al. |
| 2016/0220573 A1 | 8/2016 | Di Paolo et al. |
| 2016/0310490 A1 | 10/2016 | Blomgren et al. |
| 2016/0368918 A1 | 12/2016 | Blomgren et al. |
| 2016/0375019 A1 | 12/2016 | Di Paolo et al. |
| 2017/0020821 A1 | 1/2017 | Casteel et al. |
| 2017/0035755 A1 | 2/2017 | Blomgren et al. |
| 2017/0095490 A1 | 4/2017 | Blomgren et al. |
| 2017/0121350 A1 | 5/2017 | Blomgren et al. |
| 2017/0217967 A1 | 8/2017 | Elford et al. |
| 2017/0258804 A1 | 9/2017 | Di Paolo et al. |

FOREIGN PATENT DOCUMENTS

| | | |
|---|---|---|
| EP | 480713 A1 | 4/1992 |
| JP | 2001-302667 A | 10/2001 |
| JP | 2004-528295 A | 9/2004 |
| JP | 2005-530739 A | 10/2005 |
| JP | 2008-519843 A | 6/2008 |
| JP | 2011-511835 A | 4/2011 |
| NZ | 593460 A | 11/2013 |
| WO | WO-1988/04298 A1 | 6/1988 |
| WO | WO-1995/12594 A1 | 5/1995 |
| WO | WO-1996/04298 A1 | 2/1996 |
| WO | WO-1996/34866 A1 | 11/1996 |

(56) References Cited

FOREIGN PATENT DOCUMENTS

| | | |
|---|---|---|
| WO | WO-1999/28322 A1 | 6/1999 |
| WO | WO-2001/27119 A2 | 4/2001 |
| WO | WO-2001/27119 A3 | 4/2001 |
| WO | WO-2001/83485 A1 | 11/2001 |
| WO | WO-2002/10170 A1 | 2/2002 |
| WO | WO-2002/30428 A1 | 4/2002 |
| WO | WO-2002/060492 A1 | 8/2002 |
| WO | WO-2002/066481 A1 | 8/2002 |
| WO | WO-2002/076985 A1 | 10/2002 |
| WO | WO-2003/070732 A1 | 8/2003 |
| WO | WO-2003/089434 A2 | 10/2003 |
| WO | WO-2003/089434 A3 | 10/2003 |
| WO | WO-2004/022562 A1 | 3/2004 |
| WO | WO-2004/026310 A1 | 4/2004 |
| WO | WO-2004/026867 A2 | 4/2004 |
| WO | WO-2004/026867 A3 | 4/2004 |
| WO | WO-2004/026877 A1 | 4/2004 |
| WO | WO-2004/072080 A1 | 8/2004 |
| WO | WO-2004/072081 A1 | 8/2004 |
| WO | WO-2005/005429 A1 | 1/2005 |
| WO | WO-2005/014599 A1 | 2/2005 |
| WO | WO-2005/019220 A2 | 3/2005 |
| WO | WO-2005/019220 A3 | 3/2005 |
| WO | WO-2005/047290 A2 | 5/2005 |
| WO | WO-2005/047290 A3 | 5/2005 |
| WO | WO-2005/085252 A1 | 9/2005 |
| WO | WO-2006/044687 A2 | 4/2006 |
| WO | WO-2006/044687 A3 | 4/2006 |
| WO | WO-2006/053121 A2 | 5/2006 |
| WO | WO-2006/053121 A3 | 5/2006 |
| WO | WO-2008/025821 A1 | 3/2008 |
| WO | WO-2008/057512 | 5/2008 |
| WO | WO-2009/077334 A1 | 6/2009 |
| WO | WO-2009/102468 A1 | 8/2009 |
| WO | WO-2010/006947 A1 | 1/2010 |
| WO | WO-2010/027500 A1 | 3/2010 |
| WO | WO-2010/068257 A1 | 6/2010 |
| WO | WO-2010/068258 A1 | 6/2010 |
| WO | WO-2011/112995 A1 | 9/2011 |
| WO | WO-2014/028665 A1 | 2/2014 |
| WO | WO-2015/017460 A1 | 2/2015 |
| WO | WO-2015/017466 A1 | 2/2015 |
| WO | WO-2015/084992 A1 | 6/2015 |
| WO | WO-2015/100217 A1 | 7/2015 |
| WO | WO-2016/010809 A1 | 1/2016 |
| WO | WO-2016/010862 A1 | 1/2016 |
| WO | WO-2016/172117 A1 | 4/2016 |
| WO | WO-2016/126552 A1 | 8/2016 |

OTHER PUBLICATIONS

Krisenko, "Calling in SYK: SYK's dual role as a tumor promoter and tumor suppressor in cancer," Biochimica et Biophysica Acta 1853 (2015), pp. 254-263. (Year: 2015).*

Examination Report in Australia Application No. 2015290000 dated May 23, 2017, 3 pages.

Examination Report in New Zealand Application No. 726365 dated May 30, 2017, 4 pages.

International Preliminary Report on Patentability in International Application No. PCT/US2015/040029 dated Jan. 17, 2017, 9 pages.

Al-Dabbagh, S. G. et al. (1984). "Species Differences in Oxidative Drug Metabolism: Some Basic Considerations." Archives of Toxicology. Supplement. Archive fur Toxikologie. Supplement, 7:219-231.

Anonymous: "NCT02404220 on Jun. 19, 2015: ClinicalTrials.gov Archive", ClinicalTrials.gov, Jun. 19, 2015, pp. 1-4, XP055213378: URL:https://clinicaltrials.gov/archive/NCT02404220/2015_06_19 [retrieved on Sep. 15, 2015] the whole document.

Anonymous: "Vinca Alkaloids for Cancer Treatment" (May 24, 2014), XP055213453, Mountain Lakes, New Jersey 07046, US. Retrieved from the Internet: URL:https://web.archive.org/web/20140524022911/http://chemoth.com/types/vinca-alkaloids [retrieved on Sep. 15, 2015] the whole document.

Bastin, J.R. et al, (2000, e-pub. Jul. 19, 2000). "Salt Selection and Optimisation Procedures for Pharmaceutical New Chemical Entities," Org. Proc. Res. Dev., 4(5):427-435.

Berge, SM. et al. (1977). "Pharmaceutical Salts," J. Pharm Sci., 66(1):1-19.

Blazer, B.R. et al. (Jun. 1, 2013). "Advance in Graft-Versus-Host Disease Biology and Therapy," Nat. Rev. Immunol., 12(6):443-458.

Bouloc, N. et al. (Oct. 15, 2010). "Structure-Based Design of Imidazo[1,2-a]Pyrazine Derivatives as Selective Inhibitors of Aurora-A Kinase in Cell," Bioorg. Med. Chem Lett., 20(20):5988-5993.

Buchner et al., "Spleen tyrosine kinase inhibition prevents chemokine- and integrin-mediated stromal protective effects in chronic lymphocytic leukemia", Blood, 2010, vol. 115, No. 22, pp. 4497-4506.

Bundgaard, H., (1985). Design of Prodrugs, Elsevier Science Publishers, B.V., The Netherlands, p. 1.

Burke et al., "Allosteric activation of Pl3Ka by oncogenic mutations", Oncotarget, 2013, vol. 4, No. 2, pp. 180-181.

Clinicaltrials.gov/ct2/show/NTC01799889 Jul. 3, 2013.

Currie et al., Discovery of GS-9973, a Selective and Orally Efficacious Inhibitor of Spleen Tyrosine Kinase, J. Med. Chem., 2014, vol. 57, pp. 3856-3873.

Currie, K. et al. (2014) "Discovery of GS-9973, a Selective and Orally Efficacious Inhibitor of Spleen Tyrosine Kinase" Journal of Medicinal Chemistry, vol. 57, No. 9, pp. 3856-3873.

Dean, D.C. (2000). "Recent Advances in the Synthesis and Applications of Radiolabeled Compounds for Drug Discovery and Development," Curr. Pharm Des. 6(10):Preface, 1 page.

Ding, S. et al. (2002) "A Combinatorial Scaffold Approach Toward Kinase-Directed Heterocycle Libraries," J. Am Chem Soc., 124(8):1594-1596.

Elder, DP.et al, (2010). "The Utility of Sulfonate Salts in Drug Development," J Pharm Sci, 99(7):2948-2961.

European Communication dated Jun. 18, 2013, for EP Patent Application No. 11 709 600.8 filed on Mar. 11, 2011, 6 pages.

European Communication dated Jun. 6, 2013, for EP Patent Application No. 09 832 228.2 filed on Jun. 21, 2011, 5 pages.

European Communication dated Oct. 24, 2012, for European Patent Application No. 09710901.1, filed on Feb. 12, 2009, five pages.

Evans, E.A. (1981). "Synthesis of Radiolabeled Compounds," J. Radioanal. Chem. 64(1-2):9-32.

Extended European Search Report dated Apr. 26, 2012, for European Patent Application No. 09 83 2229.0, filed on Jun. 21, 2011, 6 pages.

Extended European Search Report dated Jul. 27, 2012, for European Patent Application No. 09 83 2228.2, filed on Jun. 21, 2011, 12 pages.

Final Office Action dated Dec. 10, 2015, for U.S. Appl. No. 14/559,707, filed Dec. 3, 2014, 11 pages.

Hackam, DG et al. (2006). "Translation of Research Evidence from Animals to Humans," JAMA, 296(14):1731-1732.

International Search Report dated Apr. 4, 2016, for PCT Application No. PCT/US2016/015727, internationally filed on Jan. 29, 2016, 4 pages.

International Search Report dated Feb. 11, 2015, for PCT Application No. PCT/US2015/039677, internationally filed on Jul. 9, 2015, 4 pages.

International Search Report dated Jun. 23, 2016, for PCT Application No. PCT/US2016/028303, internationally filed on Apr. 19, 2016, 4 pages.

International Search Report dated Mar. 3, 2015, for PCT Application No. PCT/US2014/068423, internationally filed on Dec. 3, 2014, 3 pages.

International Search Report dated Oct. 13, 2014, for PCT Application No. PCT/US2014/048741, internationally filed on Jul. 29, 2014, 4 pages.

International Search Report dated Oct. 8, 2014, for PCT Application No. PCT/US2014/048733, internationally filed on Jul. 29, 2014, 3 pages.

International Search Report dated Oct. 9, 2015, for PCT Application No. PCT/US2015/040029, internationally filed on Jul. 10, 2015, 5 pages.

Intl. Search Report—Written Opinion dated Oct. 9, 2015 for PCT/US2015/040029.

(56) References Cited

OTHER PUBLICATIONS

Jeffrey, T.K. et al. (1998). "Phosphodiesterase III and V Inhibitors on Pulmonary Artery from Pulmonary Hypertensive Rats: Differences Between Early and established Pulmonary Hypertension," *J. Cardiovascular Pharmacology*, 32(2): 213-219.

Jordan, V.C. (Mar. 2003). "Tamoxifen: A Most Unlikely Pioneering Medicine" *Nature Reviews: Drug Discovery* 2:205-213.

Kabalka, G.W. et al. (1989). "The Synthesis of Radiolabeled Compounds via Organometallic Intermediates," *Tetrahedron* 45(21):6601-21.

Krisenko (2015) "Calling in SYK: SYK's Dual Role as a Tumor Promoter and Tumor Suppressor in Cancer," Biochimica et Biophysica Acta 1853, pp. 254-263.

Kuhnz, W. et al. (Jun. 11, 1998). "Predicting the Oral Bioavailability of 19-Nortestosterone Progestins In Vivo From Their Metabolic Stability in Human Liver Microsomal Preparation In Vitro," *The American Society for Pharmacology and Experimental Therapeutics* 26(11)1120-1127.

Le Huu, D. et al. (2014). "Blockade of Syk Ameliorates the Development of Murine Sclerodermatous Chronic Graft-Versus-Host Disease," *Journal of Dermatological Science*, 74:214-221.

Lumma, Jr., W.C. et al. (1983) "Piperazinylimidazo [1,2-a]pyrazines with Selective affinity for in Vitro a-Adrenergic Receptor Subtypes," *J. Med. Chem.* 26(3):357-363.

Merino et al., "Bcl-2, Bcl-xL, and Bcl-w are not equivalent targets of ABT-737 and navitoclax (ABT-263) in lymphoid and leukemic cells", *Blood*, 2012, vol. 119, No. 24, pp. 5807-5816.

Non-Final Office Action dated Apr. 22, 2016, for U.S. Appl. No. 14/446,011, filed Jul. 29, 2014, 22 pages.

Non-Final Office Action dated Aug. 7, 2015, for U.S. Appl. No. 14/559,707, filed Dec. 3, 2014, 13 pages.

Non-Final Office Action dated Dec. 15, 2016, for U.S. Appl. No. 15/178,164, filed Jun. 9, 2016, 34 pages.

Non-Final Office Action dated Feb. 12, 2016, for U.S. Appl. No. 14/795,123, filed Jul. 9, 2015, 13 pages.

Non-Final Office Action dated Jan. 20, 2017, for U.S. Appl. No. 15/010,906, filed Jun. 9, 2016, 30 pages.

Non-Final Office Action dated Jun. 17, 2016, for U.S. Appl. No. 14/796,795, filed Jul. 10, 2015, 11 pages.

Non-Final Office Action dated Sep. 16, 2016, for U.S. Appl. No. 14/559,707, filed Dec. 3, 2014, 12 pages.

Oravcova, J. et al. (1996). "Drug-Protein Binding Studies New Trends in Analytical and Experimental Methodology," *J Chromatogr B* 677:1-28.

Paulekuhn et al. (2007). "Trends in Active Pharmaceutical Ingredient Salt Selection Based on Analysis of the Orange Book Database," *J Med Chem.*, 50 :6665-6672.

Roberts et al., "Molecular and functional characterization of the human platelet Na+/CA2+ exchanges", *British Journal of Pharmacology*, 2012, vol. 165, pp. 922-936.

Roberts, et al., "Substantial Susceptibility of Chronic Lymphocytic Leukemia to BCL2 Inhibition: Results of a Phase I Study of Navitoclax in Patients With Relapsed or Refractory Disease", *J. Clin. Oncol.*, 2012, vol. 30, No. 5, pp. 488-496.

Silverman, R.B. (1992), *The Organic Chemistry of Drug Design and Drug Action*, Academic.Press, Inc. San Diego, CA, pp. 352-400.

Sorensen, J. et al. (1987) "Vinca Alkaloids in the Treatment of Non-Small Cell Lung Cancer" Cancer Treatment Reviews vol. 14, No. 1, pp. 29-51.

Stenberg, K.A.E. et al., (2000). "KinMutBase, a Database of Human Disease-Causing Protein Kinase Mutations", *Nucleic Acids Research* 28(1):369-371.

Taylor, R. et al., (1984). "Hydrogen-Bond Geometry in Organic Crystals", *Acc. Chem Res.* 17:320-326.

Vitse, O. et al. (1999). "New Imidazo [1,2-α]pyrazine Derivatives with Bronchodilatory and Cyclic Nucleotide Phosphodiesterase Inhibitory Activities," *Bioorganic and Medicinal Chemistry* 7:1059-1065.

Willander, K. et al. (Jun. 2013). "NOTCH1 Mutations Influence Survival in Chronic Lymphocytic Leukemia Patients," *BMC Cancer*, 13:274, pp. 1-6.

Written Opinion dated Apr. 4, 2016, for PCT Application No. PCT/US2016/015727, internationally filed on Jan. 29, 2016, 7 pages.

Written Opinion dated Feb. 11, 2015, for PCT Application No. PCT/US2015/039677, internationally filed on Jul. 9, 2015, 7 pages.

Written Opinion dated Jun. 23, 2016, for PCT Application No. PCT/US2016/028303, internationally filed on Apr. 19, 2016, 5 pages.

Written Opinion dated Mar. 3, 2015, for PCT Application No. PCT/US2014/068423, internationally filed on Dec. 3, 2014, 5 pages.

Written Opinion dated Oct. 13, 2014, for PCT Application No. PCT/US2014/048741, internationally filed on Jul. 29, 2014, 6 pages.

Written Opinion dated Oct. 8, 2014, for PCT Application No. PCT/US2014/048733, internationally filed on Jul. 29, 2014, 5 pages.

Written Opinion dated Oct. 9, 2015, for PCT Application No. PCT/US2015/040029, internationally filed on Jul. 10, 2015, 8 pages.

Zaragoza, D.F. (2005). *Side Reactions in Organic Synthesis: A Guide to Successful Synthesis Design*, Weinheim;WILEY-VCH Verlag GmbH &Co. KGaA, Preface, 2 pages.

ClinicalTrials.gov Archive, Jun. 19, 2015, "NCT02404220" "Safety and Efficacy of Entospletinib With Vincristine and Dexamethasone in Adults With Relapsed or Refractory Acute Lymphoid Leukemia (ALL)", pp. 1-4.

Official Action for Japanese Application No. 2017-501698 dated Sep. 20, 2017. (10 pages).

* cited by examiner

COMBINATION METHODS FOR TREATING CANCERS

CROSS REFERENCE TO RELATED APPLICATIONS

This application is a Continuation of U.S. application Ser. No. 14/796,795, filed on Jul. 10, 2015, now U.S. Pat. No. 9,707,236, which claims priority to and the benefit of U.S. Provisional Application No. 62/024,424, filed on Jul. 14, 2014, which is hereby incorporated by reference in its entirety.

FIELD

The present disclosure relates generally to the field of therapeutics and medicinal chemistry, and more specifically to the use of certain Spleen Tyrosine Kinase (Syk) inhibitors in combination with the use of certain vinca-alkaloids in the treatment of cancer including, for example, leukemia, lymphoma and solid-cell tumors.

BACKGROUND

A number of imidazopyrazine compounds are under investigation for inhibiting Spleen Tyrosine Kinase (Syk) activity. Syk is a non-receptor tyrosine kinase that plays critical roles in immunoreceptor- and integrin-mediated signaling in a variety of cell types, including B-cells, macrophages, monocytes, mast cells, eosinophils, basophils, neutrophils, dendritic cells, T-cells, natural killer cells, platelets, and osteoclasts.

Syk has been reported to play an important role in signaling through the B-cell receptor, known to be an important survival signal in B-cells. As such, inhibition of Syk activity may be useful for treating certain types of hematologic malignancies. Examples of such hematologic malignancies include cancer, such as B-cell lymphoma and leukemia. Furthermore, there are reports of Syk expression in certain solid cancer (tumor) cell lines. Examples of such solid cancer tumors include pancreatic cancer, lung cancer, colon and colo-rectal cancer, ovarian cancer and hepatocellular cancer. Additionally, the inhibition of Syk activity is believed to be useful for treating of other diseases and conditions, including inflammatory diseases (e.g., rheumatoid arthritis), allergic disorders and autoimmune diseases.

One such compound that has been found to inhibit Syk activity is represented by formula I:

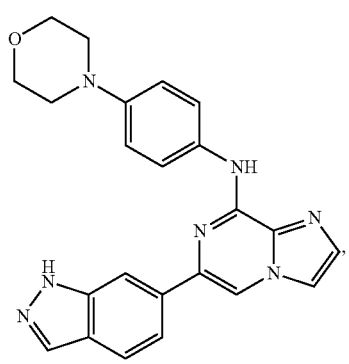
(I)

or a pharmaceutically acceptable salt thereof. The compound of formula has the chemical name 6-(1H-indazol-6-yl)-N-(4-morpholinophenyl)imidazo[1,2-a]pyrazin-8-amine. This compound and its synthesis have been described in U.S. Pat. Nos. 8,450,321 and 8,455,493, which are hereby incorporated by reference in their entirety and specifically with respect to the method of making this compound. See e.g., U.S. Pat. No. 8,450,321, Examples 1 and 2.

Vinca-alkaloids are a subset of drugs derived from the Madagascar periwinkle plant that were discovered in the 1950's, and have a variety of uses from treating diabetes, high blood pressure, and cancer. There are approximately 10 (ten) vinca-alkaloids either currently in use or in development for these indications, including the four major vinca-alkaloids in clinical oncology use: vinblastine, vinorelbine, vincristine, and vindesine. Each of these major vinca-alkaloids has been reported to cause serious side effects, most notably neuropathy. One of the more commonly known vinca-alkaloids is vincristine (VCR), also known as leurocristine and marketed as Oncovin. As with other vinca-alkaloids, vincristine is useful in cancer chemotherapy as a mitotic inhibitor and is commonly used in the standard of care regimen CHOP (Cyclophosphamide, Hydroxydaunorubicin (also known as doxyrubicin), Oncovin (vincristine) and Prednisone) for non-Hodgkin's disease or R-CHOP (CHOP in combination with Rituxan® (also known as rituximab) for B-cell lymphomas. However, vincristine also shares several serious side effects with the other vinca-alkaloids, the most serious of which is chemotherapy-induced peripheral neuropathy, a progressive, enduring, often irreversible neuropathy. This neuropathy can be so severe as to result in the reduction or even cessation of use of vincristine.

What is desired are methods for treating diseases responsive to the inhibition of Syk in subjects in need of such treatment, including in subjects who may be considered at risk for the disease, are refractory to standard treatments, and/or are in relapse after standard treatments, wherein a treatment regimen of a Syk inhibitor alone does not result in inhibition of cell activity, especially for subjects who may be sensitive to neuropathy secondary to standard dosing levels of vincristine or vinca-alkaloid containing treatment regimens.

SUMMARY

Provided herein are methods for treating cancer in a subject in need thereof, comprising administering to the subject a therapeutically effective amount of a compound of formula I:

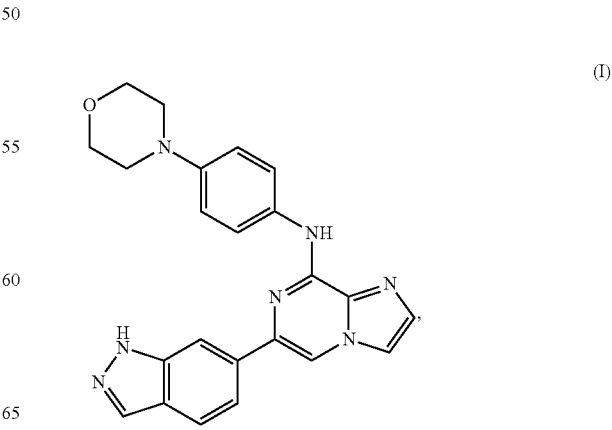
(I)

or a pharmaceutically acceptable salt thereof, in combination with a vinca-alkaloid, or a pharmaceutically acceptable salt thereof.

In some embodiments, the subject is a human who has a cancer responsive to Syk activity. In another embodiment, the subject is a human who has a solid cancer tumor which expresses Syk. In some embodiments, the subject is a human who has a 17p deletion, a TP53 mutation, NOTCH1, a SF3B1 mutation, a 11q deletion, or any combination thereof. In one embodiment, the subject is a human who has a 17p deletion, a TP53 mutation, or a combination thereof. In another embodiment, the subject is a human who has NOTCH1, a SF3B1 mutation, a 11q deletion, or any combination thereof.

In some embodiments, the vinca-alkaloid is selected from the group consisting of vincristine, vinblastine, vindesine, vinorelbine, desoxyvincaminol, vincaminol, vinburnine, vincamajine, and vineridine, and pharmaceutically acceptable salts thereof. In certain embodiments, at least one vinca-alkaloid is selected from the group consisting of vincristine, vinblastine, vindesine, vinorelbine, desoxyvincaminol, vincaminol, vinburnine, vincamajine, and vineridine and pharmaceutically acceptable salts thereof. In some embodiments, the vinca-alkaloid is selected from the group consisting of vincristine, vinblastine, vindesine, and vinorelbine, and pharmaceutically acceptable salts thereof. In other embodiments, the vinca-alkaloid is selected from the group consisting of vincristine and vinblastine, and pharmaceutically acceptable salts thereof. In one embodiment, the vinca-alkaloid is vincristine and pharmaceutically acceptable salts thereof. In another embodiment, the vinca-alkaloid is vinblastine and pharmaceutically acceptable salts thereof.

Provided herein are also methods for treating cancer in a subject in need thereof, comprising administering to the subject a therapeutically effective amount of a compound of formula I, or a pharmaceutically acceptable salt thereof, and a therapeutically effective amount of a vinca-alkaloid, or a pharmaceutically acceptable salt thereof.

Provided herein are also methods for treating cancer in a subject in need thereof, comprising administering to the subject a therapeutically effective amount of a compound of formula I, or a pharmaceutically acceptable salt thereof, and a therapeutically effective amount of a vinca-alkaloid, or a pharmaceutically acceptable salt thereof, wherein: the subject is a human who is not undergoing any other anti-cancer treatments; and the subject is (i) refractory to at least one anti-cancer treatment, or (ii) in relapse after treatment with at least one anti-cancer therapy, or a combination thereof.

Provided herein are also figures and examples illustrating that the combination of the compound of formula I, or a pharmaceutically acceptable salt thereof, and a therapeutically effective amount of a vinca-alkaloid, or a pharmaceutically acceptable salt thereto, has unexpected improvements over the effects of the compound of formula I, or the vinca-alkaloid, alone in monotherapy or administered as a sole agent in the treatment of certain cancers and their respective cell lines.

In some embodiments, the subject is not undergoing any other anti-cancer treatments using one or more PI3K inhibitors. Such PI3K inhibitors may include, in certain embodiments, Compounds A, B and C, whose structures are provided below.

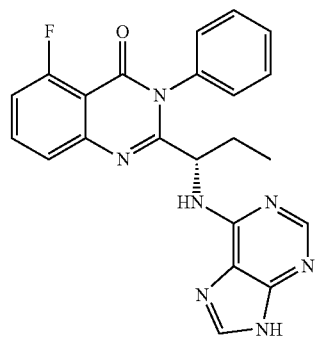

Compound A

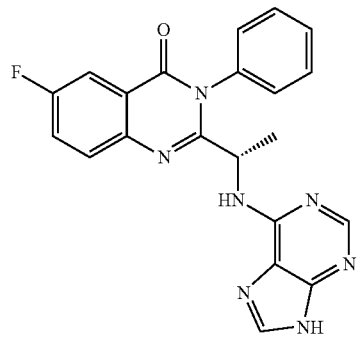

Compound B

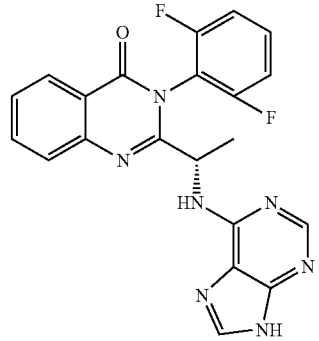

Compound C

Compound A has the chemical name (S)-2-(1-((9H-purin-6-yl)amino)propyl)-5-fluoro-3-phenylquinazolin-4(3H)-one, Compound B is named (S)-2-(1-((9H-purin-6-yl)amino)ethyl)-5-fluoro-3-phenylquinazolin-4(3H)-one, and Compound C is (S)-2-(1-((9H-purin-6-yl)amino)ethyl)-3-(2,6-difluorophenyl)quinazolin-4(3H)-one.

In some embodiments, the subject is refractory to at least one anti-cancer treatment. In other embodiments, the subject is in relapse after treatment with at least one anti-cancer treatment.

In some embodiments, about 100 mg to 800 mg of the compound of formula I, or a pharmaceutically acceptable salt thereof, is administered to subject twice daily. In other embodiments, about 200 mg to 400 mg of the compound of formula I, or a pharmaceutically acceptable salt thereof, is administered to the subject twice daily. In one embodiment, about 400 mg of the compound of formula I, or a pharmaceutically acceptable salt thereof, is administered to subject twice daily.

In one variation, the subject is a human who has a 17p deletion, a TP53 mutation, or a combination thereof; and about 100 mg to 800 mg of the compound of formula I, or a pharmaceutically acceptable salt thereof, is administered to the subject twice daily. In another variation, the subject is a human who has a 17p deletion, a TP53 mutation, or a combination thereof; and about 200 mg to 400 mg of the compound of formula I, or a pharmaceutically acceptable salt thereof, is administered to the subject twice daily. In yet another variation, the subject is a human who has a 17p deletion, a TP53 mutation, or a combination thereof; and about 400 mg of the compound of formula I, or a pharmaceutically acceptable salt thereof, is administered to the subject twice daily.

In other embodiments, the vinca-alkaloid, or a pharmaceutically acceptable salt thereof, is administered to the subject once a week at clinically approved or sub-clinically approved amounts. In some embodiments, the amount of the vinca-alkaloid is administered to the subject once a week at a sub-clinically approved amount. In other embodiments, the vinca-alkaloid is vincristine and the amount of vincristine, or a pharmaceutically acceptable salt thereof, is administered at a dose between 0.1 mg-$M^2$ and 1.5 mg-$M^2$. In other embodiments, the vinca-alkaloid is administered to the subject once a week at a dose of between 0.25 mg-M2 and 1.0 mg-M2 and the vinca-alkaloid is selected from the group consisting of vincristine and vinblastine. In other embodiments, the vinca-alkaloid is administered to the subject once daily at a dose of between 0.1 mg-M2 and 0.2 mg-M2 and the vinca-alkaloid is selected from the group consisting of vincristine and vinblastine.

In certain embodiments, the compound of formula (I) or a pharmaceutically acceptable salt thereof is administered before the vinca-alkaloid, or a pharmaceutically acceptable salt thereof. In other embodiments, the vinca alkaloid, or a pharmaceutically acceptable salt thereof, is administered before the compound of formula (I) or a pharmaceutically acceptable salt thereof.

In one embodiment, the compound of formula (I) or a pharmaceutically acceptable salt thereof, and the vinca-alkaloid, or a pharmaceutically acceptable salt thereof, are administered simultaneously, wherein the vinca-alkaloid is administered via IV and the compound of formula I is administered via tablet. In certain embodiments, the compound of formula I and the at least one vinca-alkaloid, or pharmaceutically acceptable salts thereof, is independently administered twice a day. In other embodiments, the compound of formula (I) or a pharmaceutically acceptable salt thereof, and the vinca-alkaloid, or a pharmaceutically acceptable salt thereof, are administered once a day. In other embodiments, the compound of formula (I) or a pharmaceutically acceptable salt thereof, and the vinca-alkaloid, or a pharmaceutically acceptable salt thereof, are administered once a week. In one embodiment, the compound of formula (I) or a pharmaceutically acceptable salt thereof, is administered twice a day, and the vinca-alkaloid, or a pharmaceutically acceptable salt thereof, is administered once a week. In one embodiment, the compound of formula (I) or a pharmaceutically acceptable salt thereof, is administered once a day, and the vinca-alkaloid, or a pharmaceutically acceptable salt thereof, is administered once a week In some embodiments, the cancer is a hematologic malignancy. In certain embodiments, the cancer is a leukemia. In one embodiment, the leukemia is chronic lymphocytic leukemia (CLL). In certain embodiments, the cancer is a lymphoma. In one embodiment, the lymphoma is non-Hodgkin's lymphoma (NHL). In one variation, the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and/or marginal zone lymphoma (MZL). Thus, it is understood that in one aspect the subject is a human who has a hematologic malignancy, such as leukemia or lymphoma.

In certain embodiments, the cancer is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

In some embodiments, the cancer is a solid tumor cancer (or solid cancer tumor). In certain embodiments the cancer is a solid tumor and expresses spleen tyrosine kinase (Syk) activity. In other embodiments, the solid tumor cancer is selected from the group consisting of pancreatic, lung, colorectal cancer, ovarian, breast, esophageal, adenocarcinoma and hepatocellular.

DESCRIPTION OF THE FIGURES

FIG. 2I details the inhibition effects on the combination of the compound of formula I and vincristine compared to vincristine alone in the OCI-LY7 cell line.

DETAILED DESCRIPTION

Figure 1:
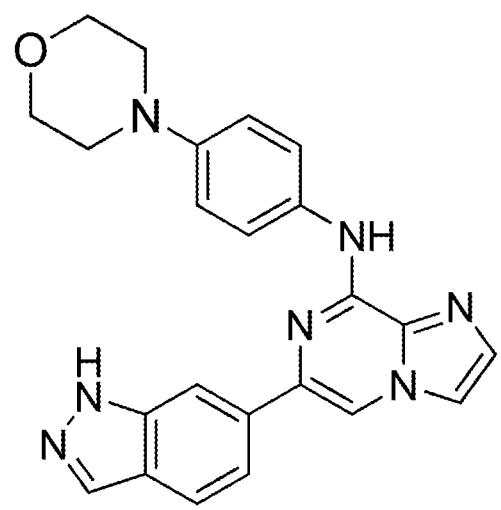
FIG. 1 depicts the chemical structure of the compound of Formula I.

The following description sets forth exemplary compositions and methods. It should be recognized, however, that such description is not intended as a limitation on the scope of the present disclosure but is instead provided as a description of exemplary embodiments.

Provided herein are methods for treating cancer in a certain population of subjects (e.g., humans) in need thereof, comprising administering to such subjects a therapeutically effective amount of a compound of formula I:

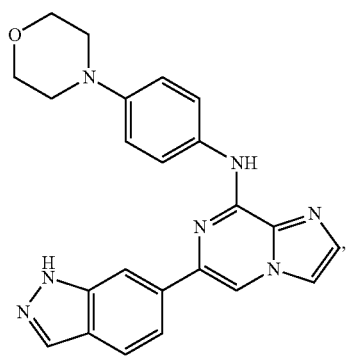

(I)

or a pharmaceutically acceptable salt, in combination with a vinca-alkaloid, or a pharmaceutically acceptable salt thereof.

Provided herein are also figures and examples illustrating that the combination of the compound of formula I, or a pharmaceutically acceptable salt thereof, and a therapeutically effective amount of a vinca-alkaloid, or a pharmaceutically acceptable salt thereto, has unexpected improvements over the effects of the compound of formula I, or the vinca-alkaloid, alone in monotherapy or administered as a sole agent in the treatment of certain cancers and their respective cell lines.

The compound of formula I may also be referred to by its compound name: 6-(1H-indazol-6-yl)-N-(4-morpholinophenyl)imidazo[1,2-a]pyrazin-8-amine. The compound name provided is named using ChemBioDraw Ultra 12.0, and one skilled in the art understands that the compound structure may be named or identified using other commonly recognized nomenclature systems and symbols including CAS and IUPAC. One method for synthesizing the compound of formula I has been previously described in, for example, U.S. Pat. No. 8,450,321.

Any formula or structure given herein, including the compound of formula I and pharmaceutically acceptable salts thereof, is also intended to represent unlabeled forms as well as isotopically labeled forms of the compounds, or salts thereof. Isotopically labeled compounds or salts thereof have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds or salts thereof of the present disclosure, for example those into which radioactive isotopes such as $^3$H, $^{13}$C and $^{14}$C are incorporated. Such isotopically labeled compounds or salts thereof may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans).

The disclosure also includes the compound of formula I and pharmaceutically acceptable salts thereof, in which from 1 to n hydrogens attached to a carbon atom is/are replaced by deuterium, in which n is the number of hydrogens in the molecule. Such compounds may exhibit increased resistance to metabolism and are thus useful for increasing the half-life of the compound of formula I, or pharmaceutically acceptable salts thereof when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of formula I and pharmaceutically acceptable salts thereof.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or salts thereof of this disclosure any atom specifically designated as a deuterium (D) is meant to represent deuterium.

Vinca alkaloids, and pharmaceutically acceptable salts thereof, are derived from the Madagascar periwinkle plant, and have been used to treat diabetes, high blood pressure, and various cancers. Examples of vinca-alkaloids include vincristine, vinblastine, vindesine, vinorelbine, desoxyvincaminol, vincaminol, vinburnine, vincamajine, and vineridine. Typically, there have been four major vinca alkaloids in clinical use: vinblastine, vinorelbine, vincristine, and vindesine. All vinca alkaloids are administered intravenously (IV).

The vinca-alkaloids, and pharmaceutically acceptable salts thereof, of the present disclosure are cytotoxics—they halt the division of cells and cause cell death. During cell division, vinca alkaloid molecules bind to the building blocks of a protein called tubulin, inhibiting its formation. Tubulin protein normally works in cells to create microtubules. These microtubules provide cells with both the structure and flexibility they need to divide and replicate. Without microtubules, cells cannot divide. As opposed to a Syk inhibitor, which inhibits spleen tyrosine kinase, vinca-alkaloids mechanism occupying tubulin's building block structure, thus preventing, in theory, the formation of microtubules and thus interfering with cancer cells' ability to divide.

One of the vinca-alkaloids of this disclosure, vinblastine, inhibits angiogenesis, or the process by which new blood vessels grow from pre-existing ones. Angiogenesis is an essential step in a tumor's transition to malignancy. Vinblastine is generally applied to treat Hodgkin's disease, non-Hodgkin's lymphoma, breast cancer, and germ cell tumors. Side effects of vinblastine include: toxicity to white blood cells, nausea, vomiting, constipation, dyspnea, chest or tumor pain, wheezing, and fever. Vinblastine is also occasionally associated with antidiuretic hormone secretion and angina.

Another vinca alkaloid of this disclosure is vinorelbine, which is similar in its effects to vinblastine. Vinorelbine has exhibited significant antitumor activity in patients with breast cancer and antiproliferation effects on osteosarcoma (bone tumor cells). Vinorelbine treatment can result in side effects including decreased resistance to infection, bruising or bleeding, anemia, constipation, diarrhea, nausea, numbness or tingling in the hands and feet, fatigue (also called peripheral neuropathy), and inflammation at the injection site. Less common side effects include hair loss and allergic reaction.

Another example or embodiment of the vinca alkaloids of this disclosure is vincristine, or pharmaceutically acceptable salts thereof. Vincristine has a high affinity for tubulin dimers (dimers are building blocks of a protein only two blocks long) and can attach and reattach at different sites quickly, thus in theory preventing the dimers' ability to reassemble (build) the tubules, thus destabilizing the tubulin and inhibiting microtubule formation. Vincristine is FDA approved to treat acute leukemia, rhabdomyosarcoma, neuroblastoma, Wilm's tumor, Hodgkin's disease, and other lymphomas. Vincristine's most common side effects are: peripheral neuropathy, suppression of bone marrow activity, constipation, nervous system toxicity, nausea, and vomiting, with neuropathy being the most common and serious side effect. As a result, there are reports of some subjects being treated with vincristine for oncology having had to stop vincristine treatment.

The fourth common vinca-alkaloid is vindesine, or pharmaceutically acceptable salts thereof. Vindesine has a serum half-life of only 24 hours, but similar effects (intended and side) to that of vinblastine. Vindesine is commonly administered at a dose of 3 milligrams per square meter of body surface during treatment for melanoma, lung cancers, and (combined with other drugs) uterine cancers. Additional side effects from vindesine include: anemia, blood cell toxicity, fatigue, tingling or pricking sensations in the skin, and skin toxicity Pharmaceutically Acceptable Salts In some embodiments of the methods described herein, a pharmaceutically acceptable salt of the compound of formula I is administered to the subject (e.g., a human).

As used herein, by "pharmaceutically acceptable" refers to a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable vehicles (e.g., carriers, adjuvants, and/or other excipients) have preferably met the required standards of toxicological and manufacturing testing and/or are included on the Inactive Ingredient Guide prepared by the U.S. Food and Drug administration.

"Pharmaceutically acceptable salts" include, for example, salts with inorganic acids and salts with an organic acid. Examples of salts may include hydrochlorate, phosphate, diphosphate, hydrobromate, sulfate, sulfinate, nitrate, malate, maleate, fumarate, tartrate, succinate, citrate, acetate, lactate, mesylate, p-toluenesulfonate, 2-hydroxyethylsulfonate, benzoate, salicylate, stearate, and alkanoate (such as acetate, HOOC—$(CH_2)_n$—COOH where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

The terms "effective amount", "pharmaceutically effective amount", and "therapeutically effective amount" refer to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc., of the subject to be treated. The effective amount can include a range of amounts. A pharmaceutically effective amount includes amounts of an agent which are effective when combined with other agents.

In some embodiments of the disclosure, the pharmaceutically acceptable salt of the compound of formula I is a bis-mesylate salt. In some embodiments of the disclosure, the pharmaceutically acceptable salt of the vinca-alkaloids is a sulfate salt. In some embodiments of the disclosure, the pharmaceutically acceptable salt of the compound of formula I is a bis-mesylate salt and the pharmaceutically acceptable salt of the vinca-alkaloids is a sulfate salt. In one embodiment of the disclosure, the pharmaceutically acceptable salt of the compound of formula I is a bis-mesylate salt and the vinca-alkaloid is vincristine, wherein the pharmaceutically acceptable salt is vincristine sulfate.

Pharmaceutical Compositions

In some embodiments of the methods described herein, the compound of formula I, or a pharmaceutically acceptable salt, is present in a pharmaceutical composition comprising the compound of formula I, or a pharmaceutically acceptable salt, and at least one pharmaceutically acceptable vehicle. Pharmaceutically acceptable vehicles may include pharmaceutically acceptable carriers, adjuvants and/or other excipients, and other ingredients can be deemed pharmaceutically acceptable insofar as they are compatible with other ingredients of the formulation and not deleterious to the recipient thereof.

The pharmaceutical compositions of the compound of formula I described herein can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The term "carrier" refers to diluents, disintegrants, precipitation inhibitors, surfactants, glidants, binders, lubricants, and other excipients and vehicles with which the compound is administered. Carriers are generally described herein and also in "Remington's Pharmaceutical Sciences" by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions, and the amounts of such carriers in the composition, may vary depending on the method of formulation (e.g., dry granulation formulation, solid dispersion formulation).

The term "diluent" generally refers to a substance that are used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent from a supersaturated solution. One example of a precipitation inhibitor includes hydroxypropylmethylcellulose (HPMC).

The term "surfactants" generally refers to a substance that lowers the surface tension between a liquid and a solid that could improve the wetting of the active agent or improve the solubility of the active agent. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders may include hydroxypropylcellulose, hydroxypropylmethylcellulose, povidone, copovidone, and ethyl cellulose.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

Methods of Treatment

Provided herein are methods for using a compound of formula I, or a pharmaceutically acceptable salt thereof, to selectively or specifically inhibit Syk activity therapeutically or prophylactically, in combination with a vinca-alkaloid, or pharmaceutically acceptable salt thereof, to selectively or specifically inhibit tubulin or microtubule formation therapeutically or prophylactically. The method comprises administering a compound of formula I, or a pharmaceutically acceptable salt thereof, or a pharmaceutical composition thereof, in combination with a vinca alkaloid, or a pharmaceutically acceptable salt thereof, to a subject (e.g., a human) in need thereof in an amount sufficient to inhibit Syk activity and/or inhibit tubulin or microtubule formation. The method can be employed to treat subjects (e.g., humans) suffering from, or subject to, a condition whose symptoms or pathology is mediated by Syk expression or activity.

"Treatment" or "treating" is an approach for obtaining beneficial or desired results including clinical results. Beneficial or desired clinical results may include one or more of the following:
(i) decreasing one more symptoms resulting from the disease;
(ii) diminishing the extent of the disease and/or stabilizing the disease (e.g., delaying the worsening of the disease);
(iii) delaying the spread (e.g., metastasis) of the disease;
(iv) delaying or slowing the recurrence of the disease and/or the progression of the disease;
(v) ameliorating the disease state and/or providing a remission (whether partial or total) of the disease and/or decreasing the dose of one or more other medications required to treat the disease;
(vi) increasing the quality of life, and/or
(vii) prolonging survival.

"Delaying" the development of a disease or condition means to defer, hinder, slow, retard, stabilize, and/or postpone development of the disease or condition. This delay can be of varying lengths of time, depending on the history of the disease or condition, and/or subject being treated. A method that "delays" development of a disease or condition is a method that reduces probability of disease or condition development in a given time frame and/or reduces the extent of the disease or condition in a given time frame, when compared to not using the method. Such comparisons are typically based on clinical studies, using a statistically significant number of subjects. Disease or condition development can be detectable using standard methods, such as routine physical exams, mammography, imaging, or biopsy. Development may also refer to disease or condition progression that may be initially undetectable and includes occurrence, recurrence, and onset.

The compound of formula I, or a pharmaceutically acceptable salt thereof, in combination with a vinca alkaloid, or a pharmaceutically acceptable salt thereof, may, in some embodiments, be administered to a subject (e.g., a human) who is at risk or has a family history of the disease or condition.

The term "inhibition" indicates a decrease in the baseline activity of a biological activity or process. "Inhibition of activity of Syk activity" refers to a decrease in activity of Syk as a direct or indirect response to the presence of the compound of formula I, or a pharmaceutically acceptable salt thereof, relative to the activity of Syk in the absence of such compound or a pharmaceutically acceptable salt thereof. In some embodiments, the inhibition of Syk activity may be compared in the same subject prior to treatment, or other subjects not receiving the treatment. "Inhibition of activity of tubulin formation" refers to a decrease in tubulin formation as a direct or indirect response to the presence of a vinca-alkaloid, or a pharmaceutically acceptable salt thereof, relative to the activity of tubulin formation in the absence of such vinca-alkaloid or a pharmaceutically acceptable salt thereof. In some embodiments, the inhibition of tubulin formation may be compared in the same subject prior to treatment, or other subjects not receiving the treatment.

Diseases

In some embodiments, the compound of formula I, or a pharmaceutically acceptable salt thereof, or a pharmaceutical composition thereof, in combination with a vinca-alkaloid, or a pharmaceutically acceptable salt thereof, is used in the treatment of cancer. In certain embodiments, the compound of formula I, or a pharmaceutically acceptable salt thereof, in combination with a vinca-alkaloid, or a pharmaceutically acceptable salt thereof, is used in the treatment of a hematologic malignancy. In some embodiments, the compound of formula I, or a pharmaceutically acceptable salt thereof, in combination with a vinca-alkaloid, or a pharmaceutically acceptable salt thereof, inhibits the growth or proliferation of cancer cells of hematopoietic origin. In some embodiments, the cancer cells are of lymphoid origin, and in certain embodiments, the cancer cells are related to or derived from B lymphocytes or B lymphocyte progenitors.

Hematologic malignancies amenable to treatment using the method disclosed in the present disclosure include, without limitation, lymphomas (e.g., malignant neoplasms of lymphoid and reticuloendothelial tissues, such as Burkitt's lymphoma, Hodgkins' lymphoma, non-Hodgkins' lymphomas, lymphocytic lymphomas); multiple myelomas; leukemias (e.g., lymphocytic leukemias, chronic myeloid (myelogenous) leukemias). Other cancer cells, of hematopoietic origin or otherwise, that express Syk also can be treated by administration of the polymorphs and compositions thereof described herein.

In particular embodiments, the hematologic malignancy is leukemia or lymphoma. In certain embodiments, the hematologic malignancy is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

In one embodiment, the cancer is T-cell acute lymphoblastic leukemia (T-ALL), or B-cell acute lymphoblastic leukemia (B-ALL). In another embodiment, the cancer is chronic lymphocytic leukemia (CLL). In yet another embodiment, the cancer is non-Hodgkin's lymphoma (NHL). In one embodiment, the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and marginal zone lymphoma (MZL). In one embodiment, the cancer is indolent non-Hodgkin's lymphoma (iNHL).

In some embodiments, the compound of formula I, or a pharmaceutically acceptable salt thereof, or a pharmaceutical composition thereof, in combination with a vinca-alkaloid, or a pharmaceutically acceptable salt thereof, is used in the treatment of a solid tumor cancer. In certain embodiments, the compound of formula I, or a pharmaceutically acceptable salt thereof, in combination with a vinca-alkaloid, or a pharmaceutically acceptable salt thereof, is used in the treatment of certain solid tumor cancers, such as pancreatic cancer, lung cancer, colon cancer, colo-rectal cancer, breast cancer, hepatocellular cancer. In certain embodiments, the compound of formula I, or a pharmaceutically acceptable salt thereof, in combination with a vinca-alkaloid, or a pharmaceutically acceptable salt thereof, is used in the treatment of certain solid tumor cancers which have an expression of Syk activity or in which Syk is expressed. Other solid tumor cancer cells that express Syk also can be treated by administration of the polymorphs and compositions thereof described herein.

In yet another aspect, provided are methods of treating a subject (e.g., a human) having a Syk-mediated disorder by administering a compound of formula I, or a pharmaceutically acceptable salt thereof, or a pharmaceutical composition thereof, in combination with a vinca-alkaloid, or a pharmaceutically acceptable salt thereof, to the subject. Provided are also methods of modulating Syk in a subject (e.g., a human) by administering a compound of formula I, or a pharmaceutically acceptable salt thereof, or a pharmaceutical composition thereof, in combination with a vinca-alkaloid, or a pharmaceutically acceptable salt thereof, to the subject.

In any of the methods described herein, the compound of formula I, or a pharmaceutically acceptable salt thereof, may be administered to the individual as a unit dosage, for example in the form of a tablet. In any of the methods described herein, the vinca-alkaloid, or a pharmaceutically acceptable salt thereof, may be administered to the individual via IV (intravenous) delivery.

Any of the methods of treatment provided herein may be used to treat cancer at an advanced stage. Any of the methods of treatment provided herein may be used to treat cancer at locally advanced stage. Any of the methods of treatment provided herein may be used to treat early stage cancer. Any of the methods of treatment provided herein may be used to treat cancer in remission. In some of the embodiments of any of the methods of treatment provided herein, the cancer has reoccurred after remission. In some embodiments of any of the methods of treatment provided herein, the cancer is progressive cancer.

Subjects

Any of the methods of treatment provided may be used to treat a subject who has been diagnosed with or is suspected of having cancer. "Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

In some of the embodiments of any of the methods provided herein, the subject is a human who is at risk of developing a cancer (e.g., a human who is genetically or otherwise predisposed to developing a cancer) and who has or has not been diagnosed with the cancer. As used herein, an "at risk" subject is a subject who is at risk of developing cancer (e.g., a hematologic malignancy, or a solid tumor cancer). The subject may or may not have detectable disease, and may or may not have displayed detectable disease prior to the treatment methods described herein. An at risk subject may have one or more so-called risk factors, which are measurable parameters that correlate with development of cancer, such as described herein. A subject having one or more of these risk factors has a higher probability of developing cancer than an individual without these risk factor(s).

These risk factors may include, for example, age, sex, race, diet, history of previous disease, presence of precursor disease, genetic (e.g., hereditary) considerations, and environmental exposure. In some embodiments, a subject at risk for cancer includes, for example, a subject whose relatives have experienced this disease, and those whose risk is determined by analysis of genetic or biochemical markers. Prior history of having cancer may also be a risk factor for instances of cancer recurrence.

Provided herein are methods for treating a subject (e.g., a human) who is at "very high risk" or "high risk" for cancer (e.g., a hematologic malignancy). Such subjects may be identified by the present of certain genetic deletions and/or mutations. In one aspect, a very high risk subject is a human who has a 17p deletion, a TP53 mutation, or a combination thereof. In one aspect, a high risk subject is a human who has NOTCH1, a SF3B1 mutation, a 11q deletion, or any combination thereof. Thus, it is understood that methods of treatment as detailed herein may, in some instances, employ selecting a subject who is at very high risk or at high risk for cancer by detecting the presence or absence of one or more 17p deletion, a TP53 mutation, NOTCH1, a SF3B1 mutation, a 11q deletion, or any combination thereof.

Provided herein are also methods for treating a subject (e.g., a human) who exhibits one or more symptoms associated with cancer (e.g., a hematologic malignancy or a solid tumor cancer). In some embodiments, the subject is at an early stage of cancer. In other embodiments, the subject is at an advanced stage of cancer.

Provided herein are also methods for treating a subject (e.g., a human) who is undergoing one or more standard therapies for treating cancer (e.g., a hematologic malignancy or a solid tumor cancer), such as chemotherapy, radiotherapy, immunotherapy, and/or surgery. Thus, in some foregoing embodiments, the compound of formula I, or a pharmaceutically acceptable salt thereof, in combination with a vinca-alkaloid, or a pharmaceutically acceptable salt thereof, administered before, during, or after administration of chemotherapy, radiotherapy, immunotherapy, and/or surgery.

In certain embodiments, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies).

In certain embodiments, the subject is refractory to at least one, at least two, at least three, or at least four anti-cancer therapy (including, for example, standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

For example, treatment of non-Hodgkin's lymphomas (NHL), especially of B-cell origin, include the use of monoclonal antibodies, standard chemotherapy approaches (e.g., CHOP, CVP, FCM, MCP, and the like), radioimmunotherapy, and combinations thereof, especially integration of an antibody therapy with chemotherapy. Examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD74. Examples of experimental antibody agents used in treatment of Non-Hodgkin's lymphoma/B-cell cancers include ofatumumab, ha20, PRO131921, alemtuzumab, galiximab, SGN-40, CHIR-12.12, epratuzumab, lumiliximab, apolizumab, milatuzumab, and bevacizumab. Examples of standard regimens of chemotherapy for Non-Hodgkin's lymphoma/B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R-MCP (R-MCP). Examples of radioimmunotherapy for Non-Hodgkin's lymphoma/B-cell cancers include yttrium-90-labeled ibritumomab tiuxetan, and iodine-131-labeled tositumomab.

In another example, therapeutic treatments for mantle cell lymphoma (MCL) include combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan) to form combination therapies R-CHOP, hyperCVAD-R, and R-FCM.

Other approaches include combining any of the abovementioned therapies with stem cell transplantation or treatment with ICE (iphosphamide, carboplatin and etoposide). Other approaches to treating mantle cell lymphoma includes immunotherapy such as using monoclonal antibodies like Rituximab (Rituxan). Rituximab can be used for treating indolent B-cell cancers, including marginal-zone lymphoma, WM, CLL and small lymphocytic lymphoma. A combination of Rituximab and chemotherapy agents is especially effective. A modified approach is radioimmunotherapy, wherein a monoclonal antibody is combined with a radioisotope particle, such as Iodine-131 tositumomab (Bexxar®) and Yttrium-90 ibritumomab tiuxetan (Zevalin®). In another example, Bexxar® is used in sequential treatment with CHOP. Another immunotherapy example includes using cancer vaccines, which is based upon the genetic makeup of an individual patient's tumor. A lymphoma vaccine example is GTOP-99 (MyVax®). Yet other approaches to treating mantle cell lymphoma includes autologous stem cell transplantation coupled with high-dose chemotherapy, or treating mantle cell lymphoma includes administering proteasome inhibitors, such as Velcade® (bortezomib or PS-341), or antiangiogenesis agents, such as thalidomide, especially in combination with Rituxan. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan®, Velcade® or other chemotherapeutic agents.

Other recent therapies for MCL have been disclosed (*Nature Reviews*; Jares, P. 2007). Such examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CCI-779), Everolimus (RAD001), BMS-345541, Curcumin, Vorinostat (SAHA), Thalidomide, lenalidomide (Revlimid®, CC-5013), and Geldanamycin (17-AAG).

Examples of other therapeutic agents used to treat Waldenstrom's Macroglobulinemia (WM) include perifosine, bortezomib)(Velcade®, rituximab, sildenafil citrate (Viagra®), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine I-131 tositumomab, motexafin gadolinium, arsenic trioxide, tipifarnib, autologous human tumor-derived HSPPC-96, veltuzumab, bryostatin 1, and PEGylated liposomal doxorubicin hydrochloride, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Examples of other therapeutic agents used to treat diffuse large B-cell lymphoma (DLBCL) drug therapies (*Blood* 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R-ICE.

Examples of other therapeutic agents used to treat chronic lymphocytic leukemia (CLL) (Spectrum, 2006, Fernandes, D.) include Chlorambucil (Leukeran), Cyclophosphamide (Cyloxan, Endoxan, Endoxana, Cyclostin), Fludarabine (Fludara), Pentstatin (Nipent), Cladribine (Leustarin), Doxorubicin (Adriamycin®, Adriblastine), Vincristine (Oncovin), Prednisone, Prednisolone, Alemtuzumab (Campath, MabCampath), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

In yet another aspect, provided is a method of sensitizing a subject (e.g., a human) who is (i) refractory to at least one chemotherapy treatment, or (ii) in relapse after treatment with chemotherapy, or both (i) and (ii), wherein the method comprises administering a compound of formula I, or a pharmaceutically acceptable salt thereof, or a pharmaceutical composition thereof, in combination with a vinca-alkaloid, or a pharmaceutically acceptable salt thereof, to the subject. A subject who is sensitized is a subject who is responsive to the treatment involving administration of the compound of formula I, or a pharmaceutically acceptable salt thereof, in combination with a vinca-alkaloid, or a pharmaceutically acceptable salt thereof, to the subject or who has not developed resistance to such treatment. In one embodiment of the disclosure, a subject who is sensitized is a subject who is responsive to the treatment involving administration of the compound of formula I, or a pharmaceutically acceptable salt thereof to the subject or who has not developed resistance to such treatment.

Monotherapy and Combination Therapies

Monotherapy

In one aspect, the compound of formula I, or a pharmaceutically acceptable salt thereof, in combination with a vinca-alkaloid, or a pharmaceutically acceptable salt thereof, is administered as a monotherapy (i.e. the only treatment regimen) to the subject (e.g., a human). Provided herein are methods of treatment in which the compound of formula I, or a pharmaceutically acceptable salt thereof, in combination with a vinca-alkaloid, or a pharmaceutically acceptable salt thereof, administered to a subject (e.g., a human) is the only anti-cancer therapy regimen administered to the subject. Provided herein are methods of treatment in which the compound of formula I, or a pharmaceutically acceptable salt thereof, in combination with a vinca-alkaloid, or a pharmaceutically acceptable salt thereof, administered to a subject (e.g., a human), wherein the subject is not undergoing any other anti-cancer treatments. In one variation, the subject is not undergoing any other anti-cancer treatments using one or more PI3K inhibitors. Such PI3K inhibitors may include, in certain embodiments, Compounds A, B and C, whose structures are provided below.

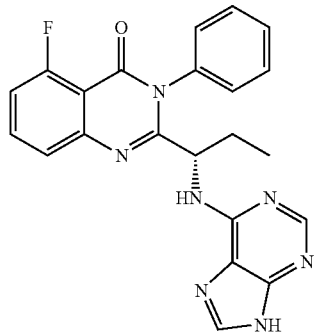

Compound A

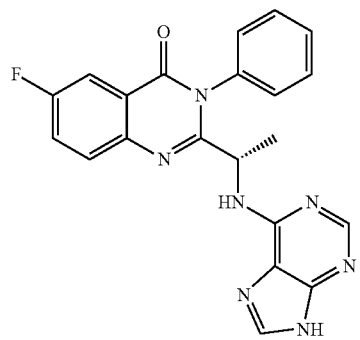

Compound B

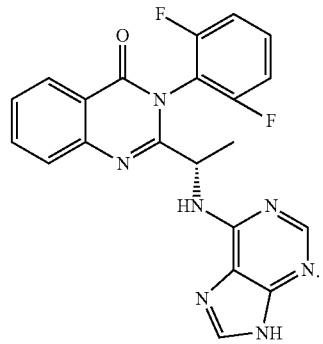

Compound C

In one variation, the subject is not undergoing any other anti-cancer treatments using Compound A, or a pharmaceutically acceptable salt thereof. In another variation, the subject is not undergoing any other anti-cancer treatments using Compound B, or a pharmaceutically acceptable salt thereof. In yet another variation, the subject is not undergoing any other anti-cancer treatments using Compound C, or a pharmaceutically acceptable salt thereof.

In some embodiments where the compound of formula I, or a pharmaceutically acceptable salt thereof, in combination with a vinca-alkaloid, or a pharmaceutically acceptable salt thereof, is administered as a monotherapy treatment regimen to the subject, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies). For example, in certain embodiments, the subject may be a human who is (i) refractory to a therapy using an anti-CD20 antibody, an alkylating agent (e.g., bendamustine), a purine analog (e.g., fludarabine), an anthracycline, or any combination thereof (ii) in relapse after treatment with an anti-CD20 antibody, an alkylating agent (e.g., bendamustine), a purine analog (e.g., fludarabine), an anthracycline, or any combination thereof, or both (i) and (ii).

A human subject who is refractory to at least one anti-cancer therapy and/or is in relapse after treatment with at least one anti-cancer therapy, as described above, may have undergone one or more prior therapies. In some embodiments, such subjects have undergone one, two, three, or four, or at least one, at least two, at least three, at least four, or at least five, or between one and ten, between one and nine, between one and eight, between one and seven, between one and six, between one and five, or between one and four, anti-cancer therapies prior to treatment using the methods described herein (e.g., prior to the administration of the compound of formula I, or a pharmaceutically acceptable salt thereof, as a monotherapy).

It should be understood that when a subject (e.g. a human) is treated with the compound of formula I, or a pharmaceutically acceptable salt thereof, in combination with a vinca-alkaloid, or a pharmaceutically acceptable salt thereof, as a monotherapy treatment regimen as described by this disclosure, the subject may also undergo one or more other therapies that are not anti-cancer therapies.

In some embodiments, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein: the vinca-alkaloid is selected from the group consisting of vincristine, vindesine, vinorelbine and vinblastine, and the subject is a human who is (i) refractory to at least one anti-cancer treatment, or (ii) in relapse after treatment with at least one anti-cancer therapy, or a combination thereof. In certain other embodiments, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein the vinca-alkaloid is selected from the group consisting of vincristine, vindesine, vinorelbine and vinblastine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In some embodiments, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein: the vinca-alkaloid is selected from the group consisting of vincristine and vinblastine, and the subject is a human who is (i) refractory to at least one anti-cancer treatment, or (ii) in relapse after treatment with at least one anti-cancer therapy, or a combination thereof. In certain other embodiments, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein the vinca-alkaloid is selected from the group consisting of vincristine and vinblastine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In one embodiment, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein: the vinca-alkaloid is vincristine, and the subject is a human who is (i) refractory to at least one anti-cancer treatment, or (ii) in relapse after treatment with at least one anti-cancer therapy, or a combination thereof. In one other embodiment, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein the vinca-alkaloid is vincristine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In one embodiment, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein: the vinca-alkaloid is vinblastine, and the subject is a human who is (i) refractory to at least one anti-cancer treatment, or (ii) in relapse after treatment with at least one anti-cancer therapy, or a combination thereof. In one other embodiment, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein the vinca-alkaloid is vinblastine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In yet other embodiments where the compound of formula I, or a pharmaceutically acceptable salt thereof, in combination with a vinca-alkaloid, or a pharmaceutically acceptable salt thereof, is administered as a monotherapy treatment regimen to the subject, the subject may have a 17p deletion, a TP53 mutation, NOTCH1, a SF3B1 mutation, a 11q deletion, or any combination thereof. In one embodiment where the compound of formula I, or a pharmaceutically acceptable salt thereof, in combination with a vinca-alkaloid, or a pharmaceutically acceptable salt thereof, is administered as a monotherapy treatment regimen to the subject, the subject has a 17p deletion, a TP53 mutation, or a combination thereof. In another embodiment where the compound of formula I, or a pharmaceutically acceptable salt thereof, in combination with a vinca-alkaloid, or a pharmaceutically acceptable salt thereof, is administered as a monotherapy treatment regimen to the subject, the subject has NOTCH1, a SF3B1 mutation, a 11q deletion, or any combination thereof.

Additional Combination Therapies

Provided herein are also methods of treatment in which the compound of formula I, or a pharmaceutically acceptable salt thereof, in combination with a vinca-alkaloid, or a pharmaceutically acceptable salt thereof, administered to a subject (e.g., a human) is given to a subject (e.g., a human) in additional combination with one or more additional therapies, including one or more of the anti-cancer therapies described above. Thus, in some embodiments, the method for treating cancer in a subject (e.g., a human) in need thereof, comprises administering to the subject a therapeutically effective amount of a compound of formula I, or a pharmaceutically acceptable salt thereof, or a pharmaceutical composition thereof, in combination with a vinca-alkaloid, or a pharmaceutically acceptable salt thereof, together with one or more additional therapies, which can be useful for treating the cancer. The one or more additional therapies may involve the administration of one or more therapeutic agents.

In some embodiments, the one or more additional therapies involve the use of a phosphatidylinositol 3-kinase (PI3K) inhibitor, including for example, Compounds A, B and C, or a pharmaceutically acceptable salt of such compounds.

In other embodiments of the methods described above involving the use of the compound of formula I, or a pharmaceutically acceptable salt thereof, in combination with a vinca-alkaloid, or a pharmaceutically acceptable salt thereof, in additional combination with one or more additional therapies, the one or more additional therapies is other than a therapy using Compound A, Compound B, or Compound C, or a pharmaceutically acceptable salt of such compounds. In one embodiment of the methods described above involving the use of the compound of formula I, or a pharmaceutically acceptable salt thereof, in combination with a vinca-alkaloid, or a pharmaceutically acceptable salt thereof, in additional combination with one or more additional therapies, the one or more additional therapies is other than a therapy using Compound A, or a pharmaceutically acceptable salt thereof. In another embodiment of the methods described above involving the use of the compound of formula I, or a pharmaceutically acceptable salt thereof, in combination with a vinca-alkaloid, or a pharmaceutically acceptable salt thereof, in additional combination with one or more additional therapies, the one or more additional therapies is other than a therapy using Compound B, or a pharmaceutically acceptable salt thereof. In yet another embodiment of the methods described above involving the use of the compound of formula I, or a pharmaceutically acceptable salt thereof, in combination with a vinca-alkaloid, or a pharmaceutically acceptable salt thereof, in additional combination with one or more additional therapies, the one or more additional therapies is other than a therapy using Compound C, or a pharmaceutically acceptable salt thereof.

In other embodiments, the one or more additional therapeutic agent may be an inhibitors of lysyl oxidase-like 2 (LOXL2) and a substance that bind to LOXL2, including for example, a humanized monoclonal antibody (mAb) with an immunoglobulin IgG4 isotype directed against human LOXL2.

In other embodiments, the one or more additional therapeutic agent may be an anti-inflammatory agent. Treatment with the one or more additional therapeutic agent may be prior to, concomitant with, or following treatment with the pharmaceutical composition described herein. In some embodiments, the pharmaceutical composition described herein, is combined with another therapeutic agent in a single dosage form, which is then administered prior to, concomitant with or subsequent to administration with a vinca-alkaloid, or a pharmaceutically acceptable salt thereof, of this disclosure. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

The compound of formula I, or a pharmaceutically acceptable salt thereof, can be useful as chemosensitizing agents, and, thus, when used in combination with a vinca-alkaloid, or a pharmaceutically acceptable salt thereof, can be useful in combination with other chemotherapeutic drugs, in particular, drugs that induce apoptosis.

A method for increasing sensitivity of cancer cells to chemotherapy, comprising administering to a subject (e.g., human) undergoing chemotherapy a chemotherapeutic agent together with a compound of formula I, or a pharmaceutically acceptable salt thereof, or a pharmaceutical composition thereof, in combination with a vinca-alkaloid, or a pharmaceutically acceptable salt thereof, in an amount sufficient to increase the sensitivity of cancer cells to the chemotherapeutic agent is also provided herein. Examples of other chemotherapeutic drugs that can be used in combination with chemical entities described herein include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine, or other vinca-alkaloids), and biological agents (e.g. antibodies such as anti CD20 antibody, IDEC 8, immunotoxins, and cytokines). In one embodiment of the method for increasing sensitivity of cancer cells to chemotherapy, the chemotherapeutic agent is other than Compound A, or a pharmaceutically acceptable salt thereof. In another embodiment of the method for increasing sensitivity of cancer cells to chemotherapy, the chemotherapeutic agent is other than Compound B, or a pharmaceutically acceptable salt thereof. In yet another embodiment of the method for increasing sensitivity of cancer cells to chemotherapy, the chemotherapeutic agent is other than Compound C, or a pharmaceutically acceptable salt thereof.

In some embodiments, the compound of formula I, or a pharmaceutically acceptable salt thereof, or a pharmaceutical composition thereof, is used in combination with Rituxan® (Rituximab) or other agents that work by selectively depleting CD20+ B-cells.

Included herein are methods of treatment in which the compound of formula I, or a pharmaceutically acceptable salt thereof, or a pharmaceutical composition thereof, in combination with a vinca-alkaloid, or a pharmaceutically acceptable salt thereof, is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate. Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates. The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one therapeutic agent is an immunosuppressant compound such as methotrexate, leflunomide, cyclosporine, tacrolimus, azathioprine, or mycophenolate mofetil are used.

It should be understood that any combinations of the additional therapeutic agents described above may be used, as if each and every combination was individually listed. For example, in certain embodiments, the additional therapeutic agents include a PI3K inhibitor and a LOXL2 inhibitor, such as simtuzumab.

Dosing Regimen and Modes of Administration

In the methods provided herein, the compound of formula I, or a pharmaceutically acceptable salt thereof, or a pharmaceutical composition thereof, is administered in a therapeutically effective amount to achieve its intended purpose. As used herein, a "therapeutically effective amount" when referring to the compound of Formula I is an amount sufficient to modulate Syk expression or activity, and thereby treat a subject (e.g., a human) suffering an indication, or to ameliorate or alleviate the existing symptoms of the indication. For example, a therapeutically effective amount of the compound of Formula I or a pharmaceutically acceptable salt thereof may be an amount sufficient to decrease a symptom of a disease or condition responsive to inhibition of Syk activity.

In the methods provided herein, the compound of formula I, or a pharmaceutically acceptable salt thereof, or a pharmaceutical composition thereof, is administered in a therapeutically effective amount to achieve its intended purpose. As used herein, a "therapeutically effective amount" when referring to a vinca-alkaloid, or a pharmaceutically acceptable salt thereof, is an amount sufficient to inhibit tubulin growth or formation, or to inhibit or reduce microtubule formation, or to interfere with spindle formation, and thereby treat a subject (e.g. a human) suffering an indication, or to ameliorate or alleviate the existing symptoms of the indication. For example, a therapeutically effective amount of a vinca-alkaloid or a pharmaceutically acceptable salt thereof may be an amount sufficient to decrease a symptom of a disease or condition responsive to inhibit of tubulin activity and/or formation.

Determination of a therapeutically effective amount is well within the capability of those skilled in the art, especially in light of the detailed disclosure provided herein. In some embodiments, a therapeutically effective amount of the compound of formula I, or a pharmaceutically acceptable salt thereof, may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

The therapeutically effective amount may vary depending on the subject, and disease or condition being treated, the weight and age of the subject, the severity of the disease or condition, and the manner of administering, which can readily be determined by one or ordinary skill in the art.

The dosing regimen of the compound of formula I, or a pharmaceutically acceptable salt thereof, in combination with a vinca-alkaloid, or a pharmaceutically acceptable salt thereof, in the methods provided herein may vary depending upon the indication, route of administration, and severity of the condition, for example. Depending on the route of administration, a suitable dose can be calculated according to body weight, body surface area, or organ size. The final dosing regimen is determined by the attending physician in view of good medical practice, considering various factors that modify the action of drugs, e.g., the specific activity of the compound, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the doses appropriate for treatment involving any of the formulations mentioned herein is done routinely by the skilled practitioner without undue experimentation, especially in light of the dosing information and assays disclosed, as well as the pharmacokinetic data observed in human clinical trials. Appropriate doses can be ascertained through use of established assays for determining concentration of the agent in a body fluid or other sample together with dose response data.

The formulation and route of administration chosen may be tailored to the individual subject, the nature of the condition to be treated in the subject, and generally, the judgment of the attending practitioner. For example, the therapeutic index of the compound of formula I, or a pharmaceutically acceptable salt thereof, may be enhanced by modifying or derivatizing the compound for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described. See e.g., Pietersz et al., Immunol. Rev., 129:57 (1992); Trail et al., Science, 261:212 (1993); and Rowlinson-Busza et al., Curr. Opin. Oncol., 4:1142 (1992). A similar analysis may be applied to treatment with the vinca-alkaloid, or its pharmaceutically acceptable salt, of this disclosure and methods herein.

Dosing Regimen

The therapeutically effective amount of the compound of formula I, or a pharmaceutically acceptable salt thereof, may be provided in a single dose or multiple doses to achieve the desired treatment endpoint. As used herein, "dose" refers to the total amount of an active ingredient (e.g., the compound of formula I, or a pharmaceutically acceptable salt thereof,) to be taken each time by a subject (e.g., a human).

Exemplary doses of the compound of formula I, or a pharmaceutically acceptable salt thereof, for a human subject may be between about 0.01 mg to about 1800 mg, or between about 0.01 mg to about 1500 mg, or between about 10 mg to about 1500 mg, or between about 10 mg to about 1300 mg, or between about 10 mg to about 1000 mg, or between about 10 mg to about 800 mg, or between about 10 mg to about 600 mg, or between about 10 mg to about 300 mg, or between about 10 mg to about 200 mg, or between about 10 mg to about 100 mg, or between about 100 mg to about 800 mg, or between about 100 mg to about 600 mg, or between about 100 mg to about 300 mg, or between about 100 mg to about 200 mg, or between about 200 mg to about 350 mg, or between about 250 mg to about 300 mg, or between about 200 mg to about 400 mg, or between about 400 mg to about 600 mg, or between about 400 mg to about 800 mg, or between about 600 mg or about 800 mg, or between about 800 mg to about 1200 mg, or between about 1200 mg to about 1600, or between about 50 mg to about 200 mg, or about 25 mg, about 50 mg, about 75 mg, about 100 mg, about 125 mg, or about 150 mg, or about 175 mg, about 200 mg, about 250 mg, about 300 mg, about 350 mg, about 400 mg, about 450 mg, about 500 mg, about 550 mg, about 600 mg, about 650 mg, about 700 mg, or about 750 mg, or about 800 mg, or about 850 mg, or about 900 mg, or about 950 mg, or about 1000 mg, or about 1100 mg, or about 1200 mg, or about 1300 mg, or about 1400 mg, or about 1500 mg, or about 1600 mg, or about 1800 mg. In one embodiment, the dose of the compound of formula I, or a pharmaceutically acceptable salt thereof, administered to the subject in the methods provided herein is about 400 mg. In one embodiment, the dose of the compound of formula I, or a pharmaceutically acceptable salt thereof, administered to the subject in the methods provided herein is about 800 mg.

In other embodiments, the methods provided comprise continuing to treat the subject (e.g., a human) by administering the doses of the compound of formula I, or a pharmaceutically acceptable salt thereof, at which clinical efficacy is achieved or reducing the doses by increments to a level at which efficacy can be maintained. In a particular embodiment, the methods provided comprise administering to the subject (e.g., a human) an initial daily dose of 100 mg to 1000 mg of the compound of formula I, or a pharmaceutically acceptable salt thereof, and administering subsequent daily doses of the compound of formula I, or a pharmaceutically acceptable salt thereof, over at least 6 days, wherein each subsequent daily dose is increased by 50 mg to 400 mg. Thus, it should also be understood that the dose of the compound of formula I, or a pharmaceutically acceptable salt thereof, may be increased by increments until clinical efficacy is achieved. Increments of about 25 mg, about 50 mg, about 100 mg, or about 125 mg, or about 150 mg, or about 200 mg, or about 250 mg, or about 300 mg can be used to increase the dose. The dose can be increased daily, every other day, two, three, four, five or six times per week, or once per week.

The frequency of dosing will depend on the pharmacokinetic parameters of the compound administered, the route of administration, and the particular disease treated. The dose and frequency of dosing may also depend on pharmacokinetic and pharmacodynamic, as well as toxicity and therapeutic efficiency data. For example, pharmacokinetic and pharmacodynamic information about the compound of formula I, or a pharmaceutically acceptable salt thereof, can be collected through preclinical in vitro and in vivo studies, later confirmed in humans during the course of clinical trials. Thus, for the compound of formula I, or a pharmaceutically acceptable salt thereof, used in the methods provided herein, a therapeutically effective dose can be estimated initially from biochemical and/or cell-based assays. Then, dosage can be formulated in animal models to achieve a desirable circulating concentration range that modulates Syk expression or activity. As human studies are conducted further information will emerge regarding the appropriate dosage levels and duration of treatment for various diseases and conditions.

Toxicity and therapeutic efficacy of the compound of formula I, or a pharmaceutically acceptable salt thereof, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The doses of such compounds lies preferably within a range of circulating concentrations that include the $ED_{50}$ with little or no toxicity.

The administration of the compound of formula I, or a pharmaceutically acceptable salt thereof, may be administered under fed conditions. The term fed conditions or variations thereof refers to the consumption or uptake of food, in either solid or liquid forms, or calories, in any suitable form, before or at the same time when the compounds or pharmaceutical compositions thereof are administered. For example, the compound of formula I, or a pharmaceutically acceptable salt thereof, may be administered to the subject (e.g., a human) within minutes or hours of consuming calories (e.g., a meal). In some embodiments, the compound of formula I, or a pharmaceutically acceptable salt thereof, may be administered to the subject (e.g., a human) within 5-10 minutes, about 30 minutes, or about 60 minutes consuming calories.

The therapeutically effective amount of the vinca-alkaloid of this disclosure, or its pharmaceutically acceptable salt thereof, may be provided in a single dose or multiple doses to achieve the desired treatment endpoint. As used herein, "dose" refers to the total amount of an active ingredient (e.g., vincristine or vinblastine, for example), or a pharmaceutically acceptable salt thereof,) to be taken each time by a subject (e.g., a human).

Exemplary doses of the vinca-alkaloid of this disclosure, or its pharmaceutically acceptable salt thereof, for a human subject may be between about 0.01 mg-$M^2$ to about 3.0 mg-$M^2$, depending on the identity of the vinca-alkaloid, or between about 0.01 mg-$M^2$ to about 2.5 mg-$M^2$, or between about 0.01 mg-$M^2$ to about 2.0 mg-$M^2$, or between about 0.01 mg-$M^2$ to about 1.9 mg-$M^2$, or between about 0.01 mg-$M^2$ to about 1.8 mg-$M^2$, or between about 0.01 mg-$M^2$ to about 1.7 mg-$M^2$, or between about 0.01 mg-$M^2$ to about 1.6 mg-$M^2$, or between about 0.01 mg-$M^2$ to about 1.5 mg-$M^2$, or between about 0.01 mg-$M^2$ to about 1.4 mg-$M^2$, or between about 0.01 mg-$M^2$ to about 1.3 mg-$M^2$, or between about 0.01 mg-$M^2$ to about 1.2 mg-$M^2$, or between about 0.01 mg-$M^2$ to about 1.1 mg-$M^2$, or between about 0.01 mg-$M^2$ to about 1.0 mg-$M^2$, or between about 0.01 mg-$M^2$ to about 0.9 mg-$M^2$, or between about 0.01 mg-$M^2$ to about 0.8 mg-$M^2$, or between about 0.01 mg-$M^2$ to about 0.7 mg-$M^2$, or between about 0.01 mg-$M^2$ to about 0.6 mg-$M^2$, or between about 0.01 mg-$M^2$ to about 0.5 mg-$M^2$, or between about 0.01 mg-$M^2$ to about 0.45 mg-$M^2$, or between about 0.01 mg-$M^2$ to about 0.4 mg-$M^2$, or between about 0.01 mg-$M^2$ to about 0.35 mg-$M^2$, or between about 0.01 mg-$M^2$ to about 0.33 mg-$M^2$, or between about 0.01 mg-$M^2$ to about 0.3 mg-$M^2$, or between about 0.01 mg-$M^2$ to about 0.25 mg-$M^2$, or between about 0.01 mg-$M^2$ to about 0.2 mg-$M^2$, or between about 0.01 mg-$M^2$ to about 0.15 mg-$M^2$, or between about 0.01 mg-$M^2$ to about 0.01 mg-$M^2$, or between about 0.1 mg-$M^2$ to about 1.8 mg-$M^2$, or between about 0.15 mg-$M^2$ to about 1.7 mg-$M^2$, or between about 0.2 mg-$M^2$ to about 1.6 mg-$M^2$, or between about 0.25 mg-$M^2$ to about 1.5 mg-$M^2$, or between about 0.3 mg-$M^2$ to about 1.4 mg-M$^2$, or between about 0.33 mg-M$^2$ to about 1.3 mg-M$^2$, or between about 0.35 mg-M$^2$ to about 1.2 mg-M$^2$, or between about 0.4 mg-M$^2$ to about 1.1 mg-M$^2$, or between about 0.45 mg-M$^2$ to about 1.0 mg-M$^2$, or between about 0.5 mg-M$^2$ to about 0.9 mg-M$^2$, or between about 0.6 mg-M$^2$ to about 0.8 mg-M$^2$. In one embodiment, the dose of the vinca-alkaloid of this disclosure, or its pharmaceutically acceptable salt thereof, administered to the subject in the methods provided herein is about 1.5 mg-M$^2$. In one embodiment, the dose of the vinca-alkaloid of this disclosure, or its pharmaceutically acceptable salt thereof, administered to the subject in the methods provided herein is about 1.0 mg-M$^2$. In one embodiment, the dose of the vinca-alkaloid of this disclosure, or its pharmaceutically acceptable salt thereof, administered to the subject in the methods provided herein is about 0.5 mg-M$^2$.

In other embodiments, the methods provided comprise continuing to treat the subject (e.g., a human) by administering the doses of the vinca-alkaloid of this disclosure, or a pharmaceutically acceptable salt thereof, at which clinical efficacy is achieved or reducing the doses by increments to a level at which efficacy can be maintained. The frequency of dosing will depend on the pharmacokinetic parameters of the compound administered, the route of administration, and the particular disease treated. The dose and frequency of dosing may also depend on pharmacokinetic and pharmacodynamic, as well as toxicity and therapeutic efficiency data.

Modes of Administration

The pharmaceutical compositions of the compound of formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the compound of formula I, or a pharmaceutically acceptable salt thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. In certain embodiments, for parenteral administration, sterile injectable solutions are prepared containing a therapeutically effective amount, e.g., 0.1 to 1000 mg, of the compound of formula I, or a pharmaceutically acceptable salt thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of the compound of formula I, or a pharmaceutically acceptable salt thereof. Administration may be via capsule or enteric coated tablets, or the like. In making the pharmaceutical compositions that include the compound of formula I, or a pharmaceutically acceptable salt thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions of the compound of formula I described herein can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

In some embodiments, the compositions of the compound of formula I described herein are formulated in a unit dosage form. The term "unit dosage forms" refers to physically discrete units suitable as unitary dosages for human subjects, each unit containing a predetermined quantity of active material calculated to produce the desired therapeutic effect, in association with a suitable pharmaceutical excipient (e.g., a tablet, capsule, ampoule).

In other embodiments, the compound of formula I, or a pharmaceutically acceptable salt thereof, or a pharmaceutical composition thereof, is administered orally at a unit dosage of about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 800 mg, about 900 mg, about 1100 mg, about 1200 mg, about 1300 mg, about 1400 mg, about 1500 mg, or about 1600 mg, about 1700 mg, or about 1800 mg. In other embodiments, the compound of formula I, or a pharmaceutically acceptable salt thereof, is administered orally at a unit dosage of about 200 mg, about 600 mg, or about 800 mg, or about 900 mg, or about 1200 mg. In some embodiments, the compound of formula I, or a pharmaceutically acceptable salt thereof, or a pharmaceutical composition thereof, is administered orally at a unit dosage of about 200 mg, or about 800 mg.

The dosages for oral administration described above for the compound of formula I may be administered once daily or twice daily (BID). For example, in certain embodiments, the compound of formula I, or a pharmaceutically acceptable salt thereof, or a pharmaceutical composition thereof, is administered orally at a unit dosage of about 50 mg BID, about 100 mg BID, about 150 mg BID, about 200 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 800 mg BID, about 900 mg BID, about 1100 mg BID, about 1200 mg BID, about 1300 mg BID, about 1400 mg BID, about 1500 mg BID, or about 1600 mg BID, about 1700 mg BID, or about 1800 mg BID. In other embodiments, the compound of formula I, or a pharmaceutically acceptable salt thereof, or a pharmaceutical composition thereof, is administered orally at a unit dosage of about 200 mg BID, about 400 mg BID, or about 600 mg BID, or about 800 mg BID, or about 1000 mg BID. In some embodiments, the compound of formula I, or a pharmaceutically acceptable salt thereof, or a pharmaceutical composition thereof, is administered orally at a unit dosage of about 200 mg BID, or about 800 mg BID. In one embodiment, the compound of formula I, or a pharmaceutically acceptable salt thereof, or a pharmaceutical composition thereof, is administered orally at a unit dosage of about 800 mg BID.

The vinca-alkaloid of the disclosure, or the pharmaceutically acceptable salts thereof, are administered via IV. In one embodiment, the vinca-alkaloid is vincristine sulfate and the amount of the vial is 1 mg/1 ml. In some embodiments, the vinca-alkaloid is vincristine sulfate and the vial is 2 ml containing either 1 mg or 2 mg of vincristine sulfate. In another embodiment, "Vincristine Sulfate", USP is a white to off-white powder. It is soluble in methanol, freely soluble in water, but only slightly soluble in 95% ethanol. In 98% ethanol, Vincristine Sulfate, USP has an ultraviolet spectrum with maxima at 221 nm ($\in$+47,100).

"Vincristine Sulfate Injection", USP is a sterile, preservative-free, single use only solution available for intravenous use in 2 mL (1 mg and 2 mg) vials. Each mL contains 1 mg Vincristine Sulfate, USP, 100 mg mannitol and Water for Injection, USP. Q.S. Sulfuric acid or sodium hydroxide have been added for pH control. The pH of Vincristine Sulfate Injection, USP ranges from 4.0 to 5.0.

Articles of Manufacture and Kits

Compositions (including, for example, formulations and unit dosages) comprising the compound of formula I, or a pharmaceutically acceptable salt thereof, can be prepared and placed in an appropriate container, and labeled for treatment of an indicated condition. Accordingly, provided is also an article of manufacture, such as a container comprising a unit dosage form of the compound of formula I, or a pharmaceutically acceptable salt thereof, and a label containing instructions for use of the compounds. In some embodiments, the article of manufacture is a container comprising a unit dosage form of the compound of formula I, or a pharmaceutically acceptable salt thereof, and at least one pharmaceutically acceptable vehicle. In another embodiment, the article of manufacture is a container comprising a unit dosage form of the compound of formula I, or a pharmaceutically acceptable salt thereof, and at least one pharmaceutically acceptable vehicle, and a vial containing a vinca-alkaloid, or a pharmaceutically acceptable salt.

Kits also are contemplated. For example, a kit can comprise unit dosage forms of the compound of formula I, or a pharmaceutically acceptable salt thereof, and a package insert containing instructions for use of the composition in treatment of a medical condition. In some embodiments, the kits comprises a unit dosage form of the compound of formula I, or a pharmaceutically acceptable salt thereof, and at least one pharmaceutically acceptable vehicle, and a vial containing a solution of vinca-alkaloid, or a pharmaceutically acceptable salt thereof. The instructions for use in the kit may be for treating a cancer, including, for example, a hematologic malignancy or solid tumor cancer malignancy. In some embodiments, the instructions for use in the kit may be for treating cancer, such as leukemia or lymphoma, including relapsed and refractory leukemia or lymphoma. In certain embodiments, the instructions for use in the kit may be for treating acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), or marginal zone lymphoma (MZL). In one embodiment, the instructions for use in the kit may be for treating chronic lymphocytic leukemia (CLL) or non-Hodgkin's lymphoma (NHL). In one embodiment, the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and marginal zone lymphoma (MZL). In one embodiment, the hematologic malignancy is indolent non-Hodgkin's lymphoma (iNHL). In certain embodiments, diseases or conditions indicated on the label can include, for example, treatment of cancer.

In certain embodiments of the article of manufacture or the kit, the unit dosage for the compound of formula I has about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 800 mg, about 900 mg, about 1100 mg, about 1200 mg, about 1300 mg, about 1400 mg, about 1500 mg, or about 1600 mg, about 1700 mg, or about 1800 mg of the compound of formula I, or a pharmaceutically acceptable salt thereof. In one embodiment, the unit dosage has about 400 mg of the compound of formula I, or a pharmaceutically acceptable salt thereof. In one embodiment of the article of manufacture or the kit, the unit dosage of the compound of formula I, or a pharmaceutically acceptable salt thereof, is a tablet.

EXAMPLES

The following examples are included to illustrate embodiments of the disclosure, and are not intended to limit the scope of the disclosure. It should be appreciated by those of skill in the art that the techniques disclosed herein represent techniques that apply in the practice of the disclosure. Those of skill in the art would appreciate that, in light of the present disclosure, changes can be made in the examples herein without departing from the spirit and scope of the disclosure.

Example 1

Effect of the Compound of Formula I Compared to Doxorubicin, Vincristine and Cyclophosphamide in 10 Diffuse Large B-Cell Lymphoma (DLBCL), 4 Multiple Myeloma (MM), 2 Follicular Lymphoma (FL), and 1 Mantle Cell Lymphoma (MCL) Cell Lines This Example evaluates the efficacy of the compound of Formula I (FIG. 1), or a pharmaceutically acceptable salt thereof, to inhibit malignant B-cell viability in 10 diffuse large B-cell lymphoma (DLBCL), 4 multiple myeloma (MM), 2 follicular lymphoma (FL), and 1 mantle cell lymphoma (MCL) cell lines. This Example also evaluates and compares the efficacy of doxorubicin, vincristine and cyclophosphamide to inhibit malignant B-cell viability in the same 10 diffuse large B-cell lymphoma (DLBCL), 4 multiple myeloma (MM), 2 follicular lymphoma (FL), and 1 mantle cell lymphoma (MCL) cell lines, to the efficacy of the compound of formula I, or a pharmaceutically acceptable salt thereof.

Cell Titer Glo Viability Assay:

All procedures were performed at Gilead Sciences, Inc. in Branford, The compound of formula (I), cyclophosphamide, doxorubicin and vincristine sulfate were dissolved in DMSO to prepare stock solutions that were serially diluted three-fold in DMSO in a 96 well plate format at 1000× so the final starting assay concentrations tested would be 10 µM, 200 µM, 10 µM, and 1 µM respectively, for each compound. Compound plates were diluted 1:100 in RPMI without serum or additives creating a 10× stock. Cells were seeded into a 96-well plate at 10,000-20,000 cells per well in 100 µl of growth media appropriate to the cell line supplemented with 100 U/L penicillin-streptomycin. OCI-Ly3, OCI-Ly4 and OCI-Ly7 were grown in Iscove's+20% FBS, OCI-Ly19 was grown in alphaMEM+20% FBS, and all other cell lines were grown in RPMI+10% FBS. To each well, 11 µl of 10× compound was added in a final concentration of 0.1% DMSO and cells were incubated at 37° C. in 5% $CO_2$ for 72 hours. Cell viability was assessed with Cell Titer Glo (Promega, Madison, Wis.) following the manufacturer's protocol on an Envision plate reader (Perkin Elmer, Waltham, Mass.). $EC_{50}$ values were determined using a four parameter variable slope model with GraphPad Prism 6.0 software. All $EC_{50}$ values represent mean values of from duplicate dose response curves. The results are reported in Table 1 below.

Table 1 summarizes the efficacy of the four compounds tested separately in the Cell Titer Glow assay for each respective cell line. The test results for the compound of formula I and the test results for cyclophosphamide did not show inhibition cell viability in any of the cell lines tested at concentrations <3000 nM and <10000 nM, respectively. Doxorubicin and vincristine $EC_{50}$ values to inhibit cell viability were calculated and ranged from 3.1-557 nM and <1 nM-103 nM respectively, as shown in Table 1.

TABLE 1

| | | Inhibition of Viability, $EC_{50}$ (nM) | | | |
|---|---|---|---|---|---|
| Cell line | Disease | Compound of Formula I | Vincristine | Doxorubicin | Cyclophosphamide |
| SU-DHL-2 | DLBCL | >3000 | 65 | 216 | >10000 |
| SU-DHL-4 | DLBCL | >3000 | 75 | 215 | >10000 |
| SU-DHL-6 | DLBCL | >3000 | 12 | 125 | >10000 |
| SU-DHL-10 | DLBCL | >3000 | 45 | 195 | >10000 |
| Karpas 422 | DLBCL | >3000 | 62 | 305 | >10000 |
| OCI-LY3 | DLBCL | >3000 | 12 | 26 | >10000 |
| OCI-LY4 | DLBCL | >3000 | <1 | 37 | >10000 |
| OCI-LY7 | DLBCL | >3000 | 4.6 | 199 | >10000 |
| OCI-LY19 | DLBCL | >3000 | 1.2 | 3.1 | >10000 |
| Pfeiffer | DLBCL | >3000 | 4.0 | 198 | >10000 |
| Mino | MCL | >3000 | 42 | 114 | >10000 |
| KMS-11 | MM | >3000 | 103 | 469 | >10000 |
| MM1.S | MM | >3000 | 59 | 66 | >10000 |
| OPM-2 | MM | >3000 | 97 | 557 | >10000 |
| RPMI-8266 | MM | >3000 | 67 | 176 | >10000 |
| WSU-FSCCL | FL | >3000 | 58 | 52 | >10000 |
| WSU-NHL | FL | >3000 | 39 | 128 | >10000 |

Example 2

Comparison Effect of the Compound of Formula I in Combination with Vincristine Versus Effect of Vincristine Alone in 10 Diffuse Large B-Cell Lymphoma (DLBCL), 4 Multiple Myeloma (MM), 2 Follicular Lymphoma (FL), and 1 Mantle Cell Lymphoma (MCL) Cell Lines This Example evaluates the efficacy of the compound of Formula I, or a pharmaceutically acceptable salt thereof, in combination with vincristine to inhibit malignant B-cell viability in 10 diffuse large B-cell lymphoma (DLBCL), 4 multiple myeloma (MM), 2 follicular lymphoma (FL), and 1 mantle cell lymphoma (MCL) cell lines. This Example also evaluates and compares the efficacy of vincristine as a single agent to inhibit malignant B-cell viability in the same 10 diffuse large B-cell lymphoma (DLBCL), 4 multiple myeloma (MM), 2 follicular lymphoma (FL), and 1 mantle cell lymphoma (MCL) cell lines, to the efficacy of the compound of formula I, or a pharmaceutically acceptable salt thereof, in combination with vincristine.

Cell Titer Glo Viability Assay:

All procedures were performed at Gilead Sciences, Inc. in Branford, Conn. Vincristine was tested alone as a single agent, or in combination with 300 nM of the compound of Formula I, at 4 concentrations within the range of 0.03-10 nM shown to be <$EC_{50}$ for cell viability as a single agent. The compound of Formula I and vincristine sulfate were dissolved in DMSO to prepare stock solutions in separate 96 well plates at 1000× for each compound so the final starting assay concentrations tested would be 300 nM for the compound of Formula I and 10 nM, 3 nM, 1 nM and 0.3 nM for vincristine. Compound plates were diluted and mixed together sequentially by 1:100 in RPMI without serum or additives creating a 10× stock in 2% DMSO of combinations or single agents. Cells were seeded into a 96-well plate at 10,000-20,000 cells per well in 100 µl of growth media appropriate to the cell line supplemented with 100 U/L penicillin-streptomycin. OCI-Ly3, OCI-Ly4 and OCI-Ly7 were grown in Iscove's+20% FBS, OCI-Ly19 was grown in alphaMEM+20% FBS, and all other cell lines were grown in RPMI+10% FBS. To each well containing cells, 11 µl of 10× compound mixture in serum-free media was added in a final concentration of 0.2% DMSO and cells were incubated at 37° C. in 5% $CO_2$ for 72 hours. Cell viability was assessed with Cell Titer Glo (CTG, Promega, Madison, Wis.) following the manufacturer's protocol on an Envision plate reader (Perkin Elmer, Waltham, Mass.). CTG signals were recorded for individual compound treatments and combinations. The results are shown in FIGS. 2A to 2Q.

Figure 2A:
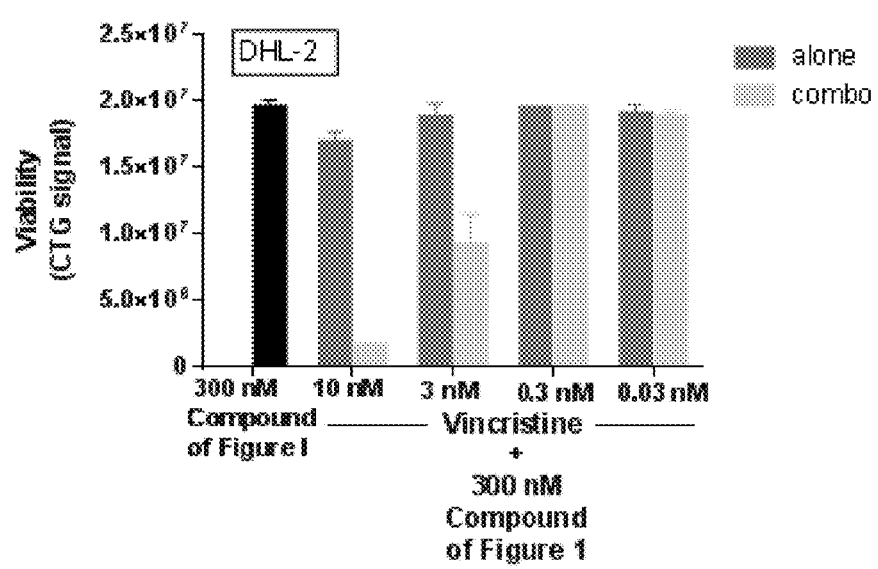
FIG. 2A details the inhibition effects on the combination of the compound of formula I and vincristine compared to vincristine alone in the DHL-2 cell line.
Figure 2B:
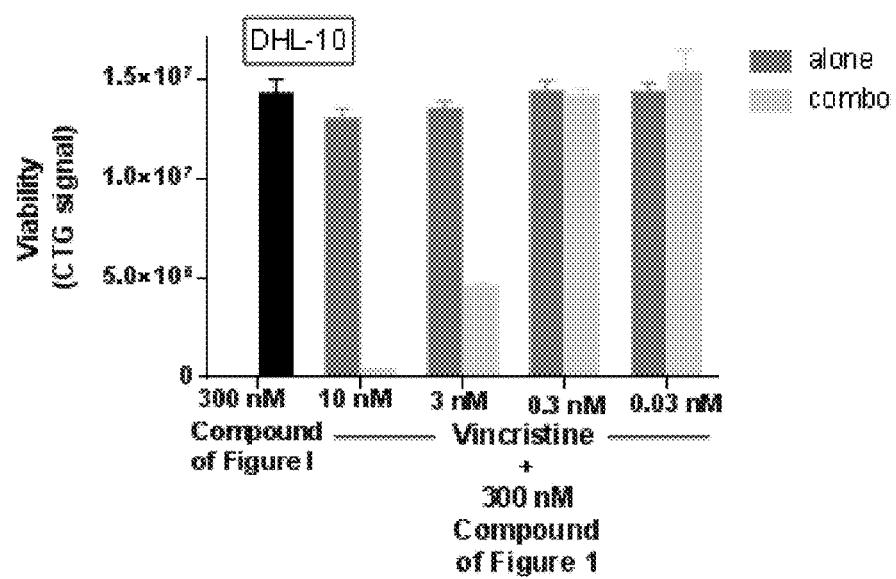
FIG. 2B details the inhibition effects on the combination of the compound of formula I and vincristine compared to vincristine alone in the DHL-10 cell line.
Figure 2C:
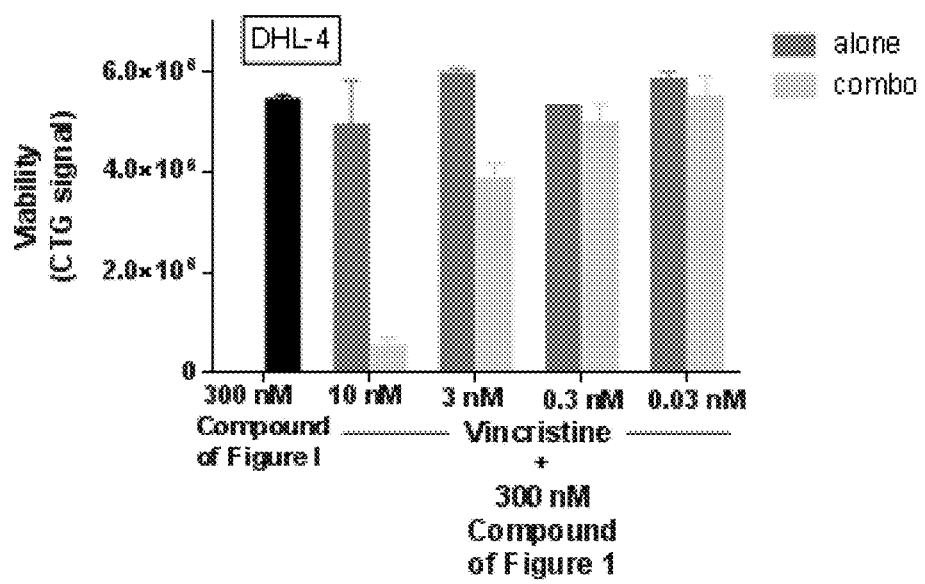
FIG. 2C details the inhibition effects on the combination of the compound of formula I and vincristine compared to vincristine alone in the DHL-4 cell line.
Figure 2D:
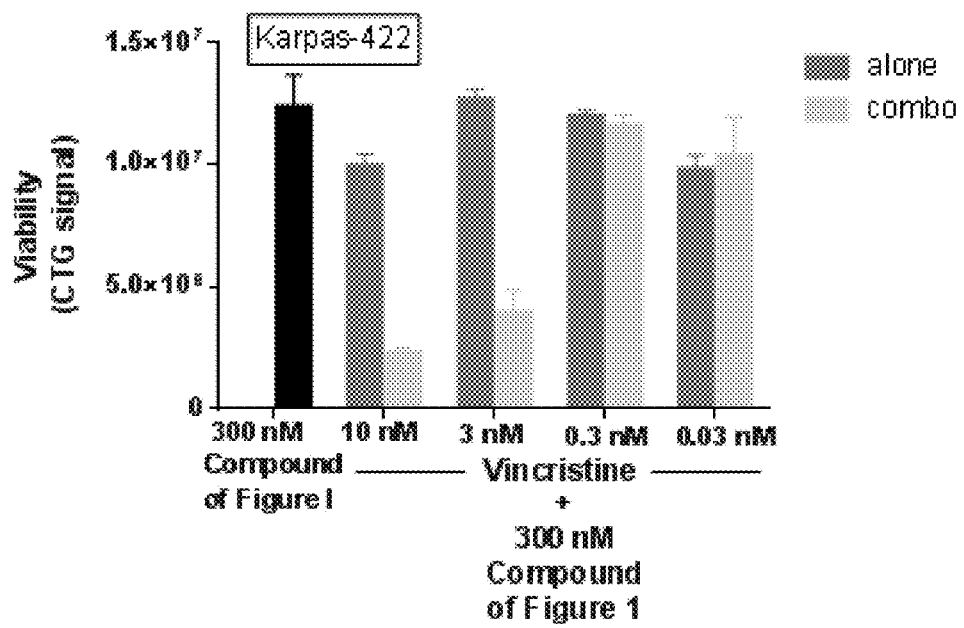
FIG. 2D details the inhibition effects on the combination of the compound of formula I and vincristine compared to vincristine alone in the Karpas-422 cell line.
Figure 2E:
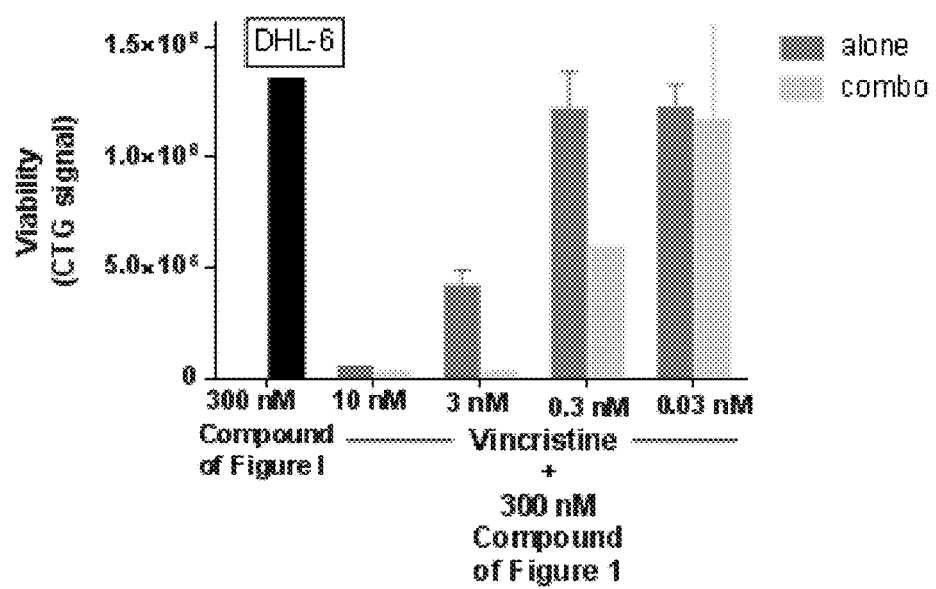
FIG. 2E details the inhibition effects on the combination of the compound of formula I and vincristine compared to vincristine alone in the DHL-6 cell line.
Figure 2F:
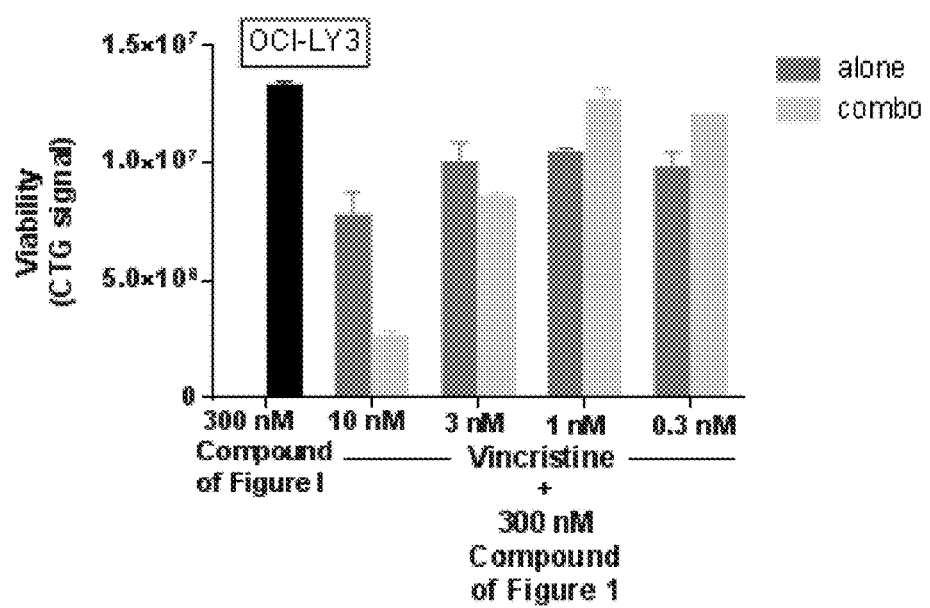
FIG. 2F details the inhibition effects on the combination of the compound of formula I and vincristine compared to vincristine alone in the OCI-LY3 cell line.
Figure 2G:
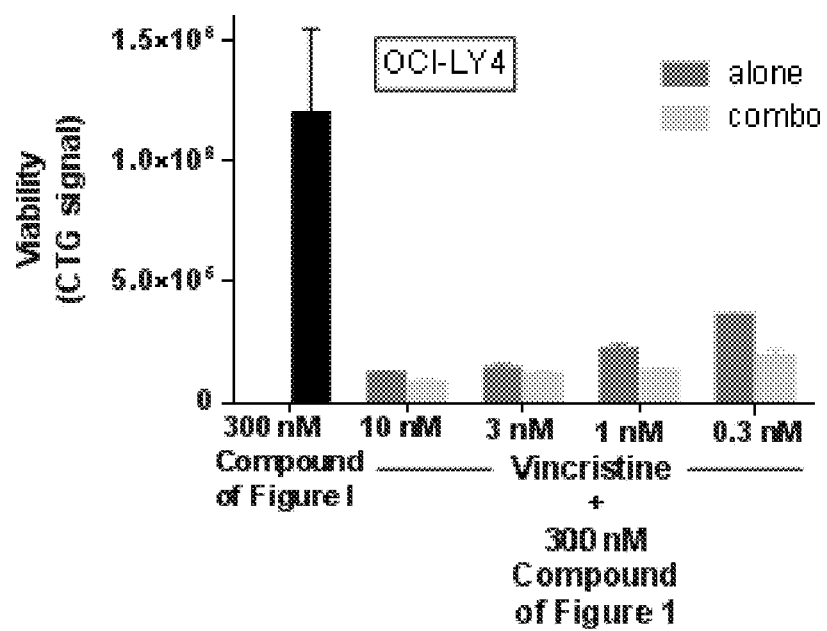
FIG. 2G details the inhibition effects on the combination of the compound of formula I and vincristine compared to vincristine alone in the OCI-LY4 cell line.
Figure 2H:
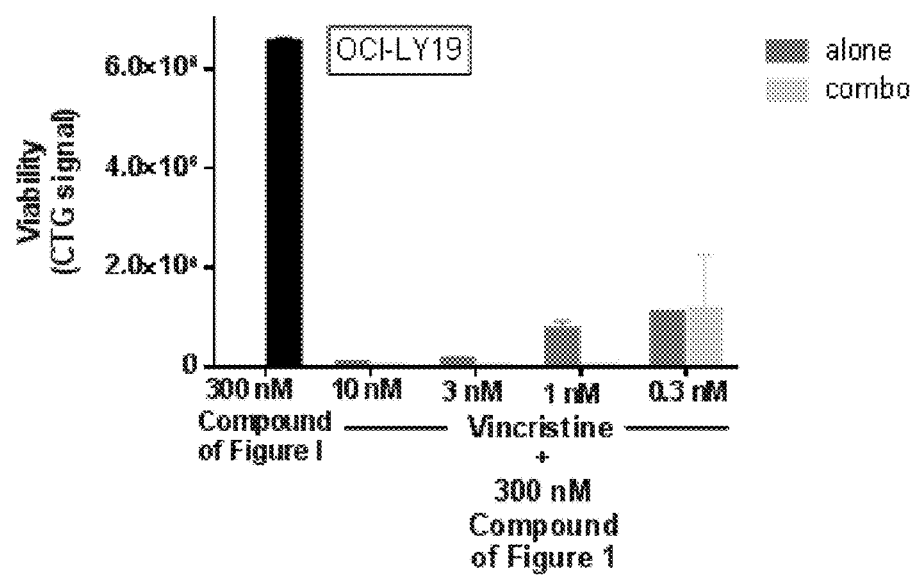
FIG. 2H details the inhibition effects on the combination of the compound of formula I and vincristine compared to vincristine alone in the OCI-LY19 cell line.
Figure 21:
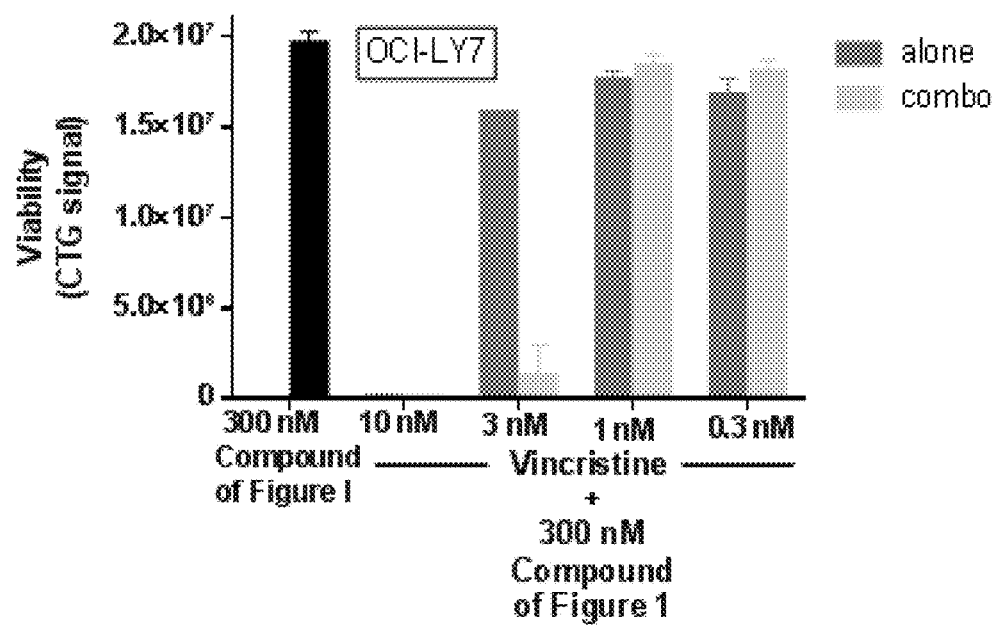
Figure 2J:
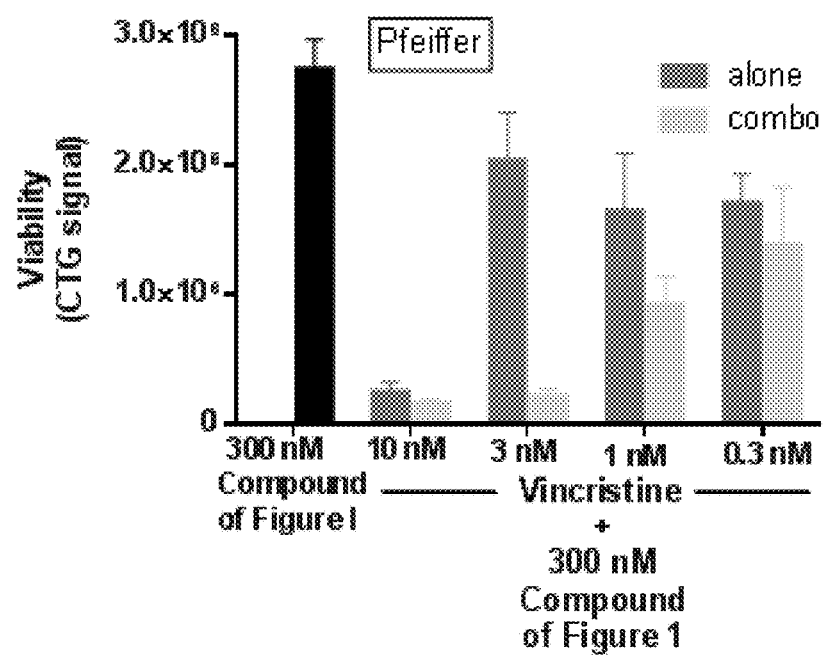
FIG. 2J details the inhibition effects on the combination of the compound of formula I and vincristine compared to vincristine alone in the Pfeiffer cell line.
Figure 2K:
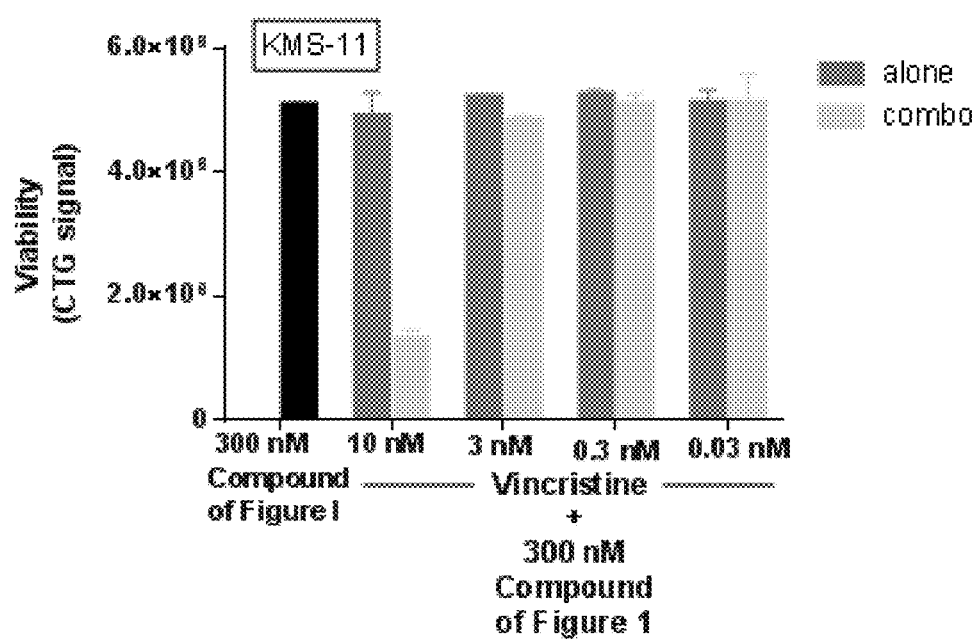
FIG. 2K details the inhibition effects on the combination of the compound of formula I and vincristine compared to vincristine alone in the KMS-11 cell line.
Figure 2L:
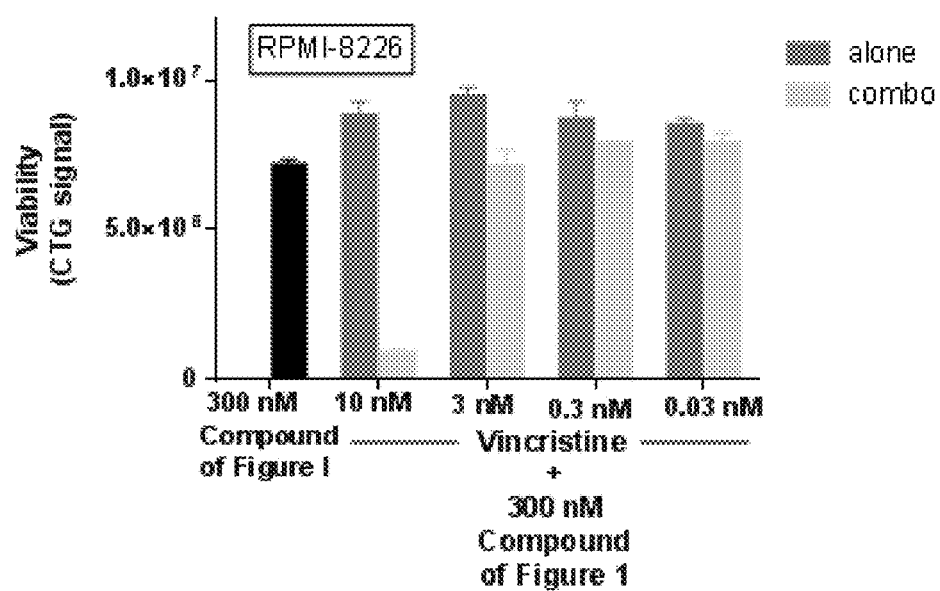
FIG. 2L details the inhibition effects on the combination of the compound of formula I and vincristine compared to vincristine alone in the RPMI-8226 cell line.
Figure 2M:
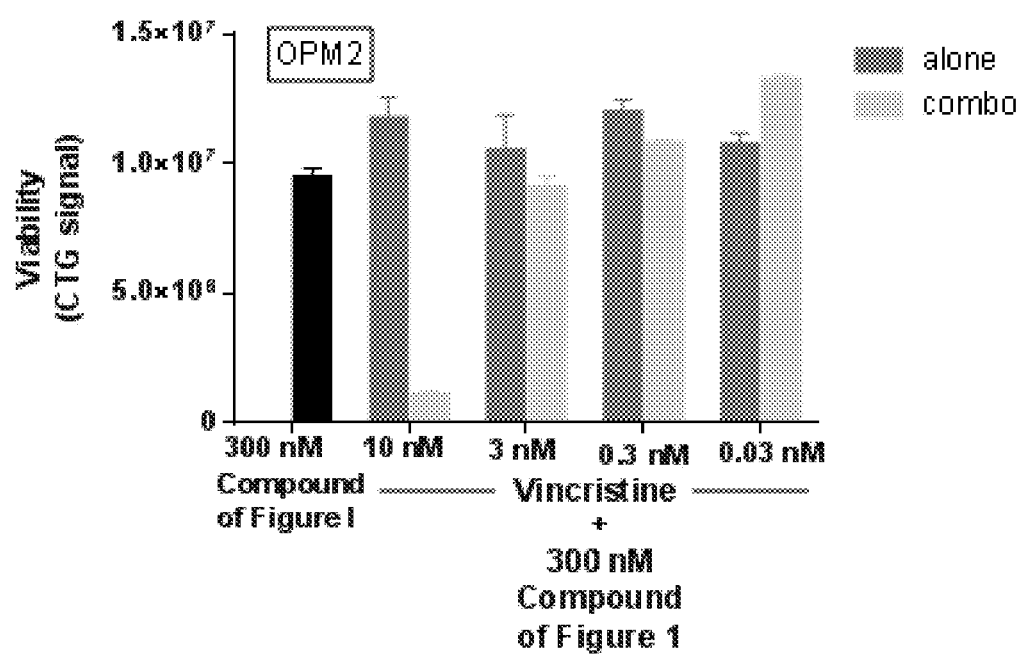
FIG. 2M details the inhibition effects on the combination of the compound of formula I and vincristine compared to vincristine alone in the OPM2 cell line.
Figure 2N:
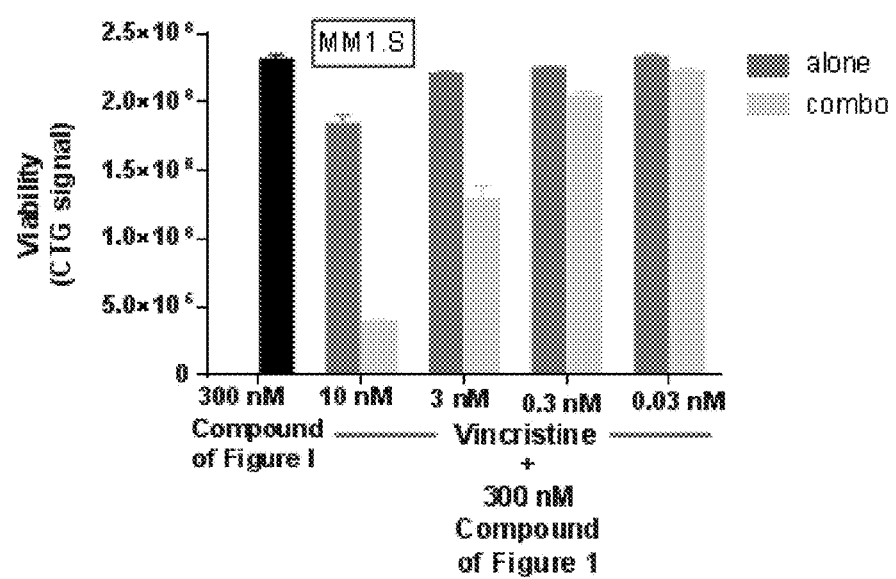
FIG. 2N details the inhibition effects on the combination of the compound of formula I and vincristine compared to vincristine alone in the MM1.S2 cell line.
Figure 2O:
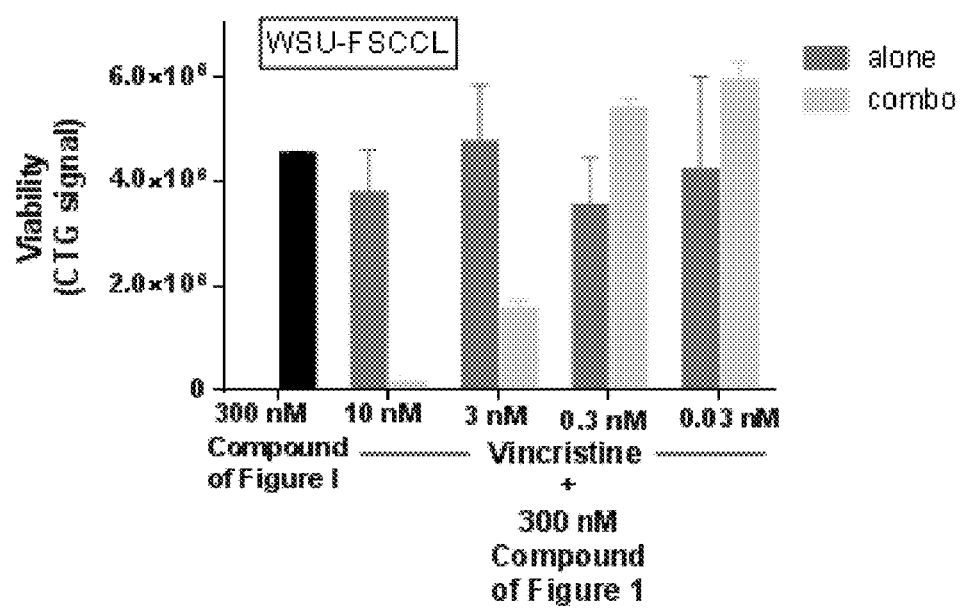
FIG. 2O details the inhibition effects on the combination of the compound of formula I and vincristine compared to vincristine alone in the WSU-FSCCL cell line.
Figure 2P:
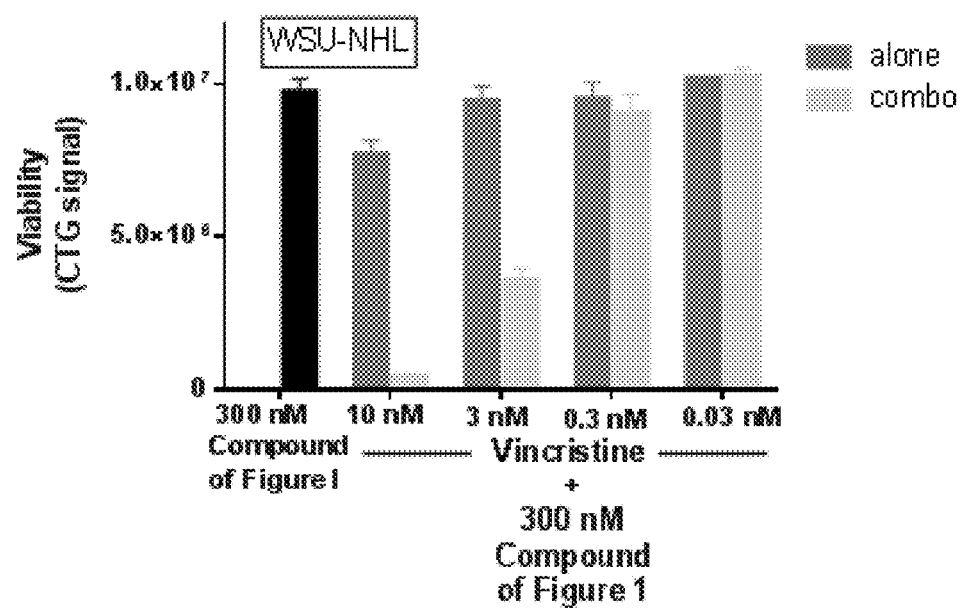
FIG. 2P details the inhibition effects on the combination of the compound of formula I and vincristine compared to vincristine alone in the WSU-NHL cell line.
Figure 2Q:
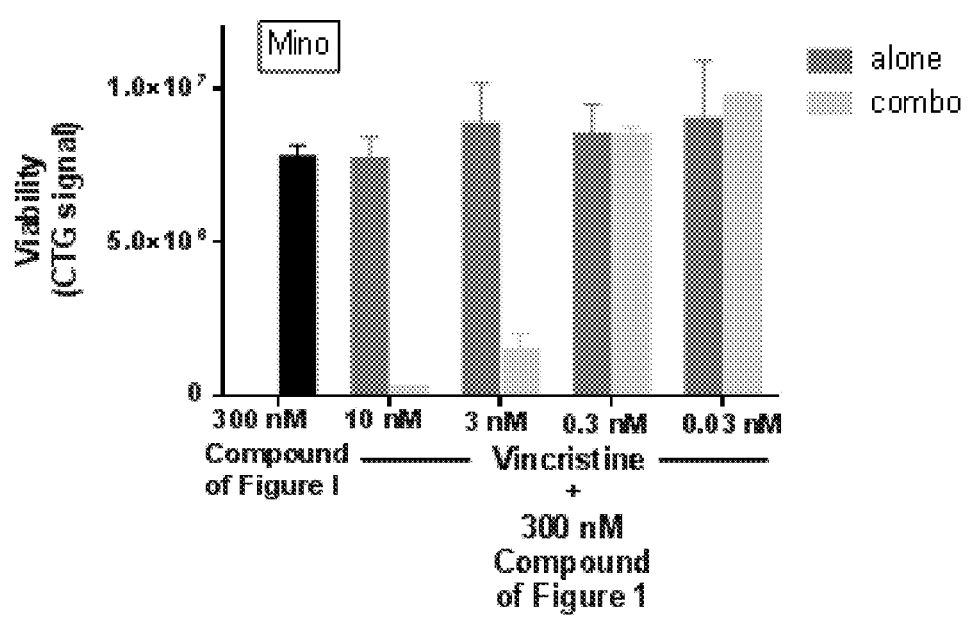
FIG. 2Q details the inhibition effects on the combination of the compound of formula I and vincristine compared to vincristine alone in the Mino cell line.

FIGS. 2A to 2Q detail the inhibition effects of the combination of the compound of formula I (FIG. 1) and vincristine as compared to vincristine alone in the 17 malignant B-cell lines, representing 4 hematological cancer types: DLBCL, MM, FL, and MCL.

Example 3

Comparison Effect of the Combination of the Compound of Formula I with Vincristine Versus Effect of the Combination of the Compound of Formula I with A) Obretastatin A4, B) Colchicine, C) Doxorubicin, and D) Taxol in the Malignant DLBCL B-Cell Line, DHL-10

This Example evaluates the efficacy of the compound of Formula I (FIG. 1), or a pharmaceutically acceptable salt thereof, in combination with vincristine to inhibit malignant B-cell viability in the malignant diffuse large B-cell lymphoma (DLBCL) cell line DHL-10. This Example also evaluates and compares the efficacy of the compound of Formula I, or a pharmaceutically acceptable salt thereof, in combination with A) cobretastatin A4, B) colchicine, C) doxorubicin and D) taxol to inhibit malignant B-cell viability in the malignant diffuse large B-cell lymphoma (DLBCL) cell line DHL-10, to the efficacy of the combination of the compound of formula I, or a pharmaceutically acceptable salt thereof, with vincristine.

Cell Titer Glo Viability Assay:

All procedures were performed at Gilead Sciences, Inc. in Branford, Conn. Vincristine, combretastatin A4, colchicine, doxorubicin, and taxol were dissolved in DMSO to prepare stock solutions that were serially diluted three-fold in DMSO in a 96 well plate format at 1000×, so the final starting assay concentrations tested would be 1 µM for all compounds except Doxorubicin which started at 10 µM. Compound plates were diluted 1:100 in RPMI without serum or additives but containing either 1% DMSO or 3 µM of the compound of Formula I creating a 10× stock. The DLBCL cell line, DHL-10 was plated at 10,000 cells per well in RPMI supplemented with 10% FBS and 100 U/L penicillin-streptomycin. To each well containing cells, 11 µl of 10× compound mixture in serum-free media was added in a final concentration of 0.2% DMSO and cells were incubated at 37° C. in 5% $CO_2$ for 72 hours. Cell viability was assessed using Cell Titer Glo (CTG, Promega, Madison, Wis.) following the manufacturer's protocol on an Envision plate reader (Perkin Elmer, Waltham, Mass.). CTG signals were recorded for individual compound treatments and combinations. $EC_{50}$ values were determined using a four parameter variable slope model with GraphPad Prism 6.0 software. Results are shown in FIG. 2. The shifts in $EC_{50}$ values for inhibition of viable DHL-10 cells for the compounds alone or in combination with 300 nM of the compound of Formula I are shown in Table 2.

Figure 3A:
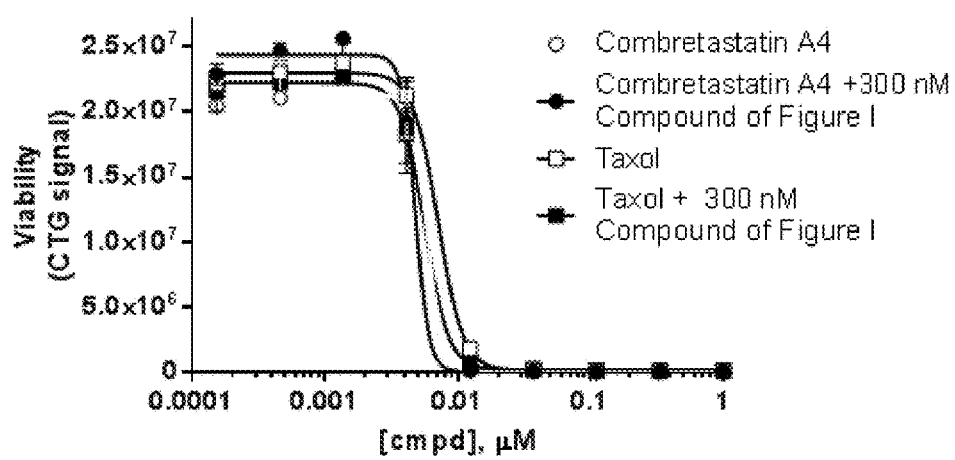
FIG. 3A summarizes the effect of the combination of the compound of Formula I and taxol versus the combination of the compound of Formula I and combretastatin A4 in the DHL-10 cell line.
Figure 3B:
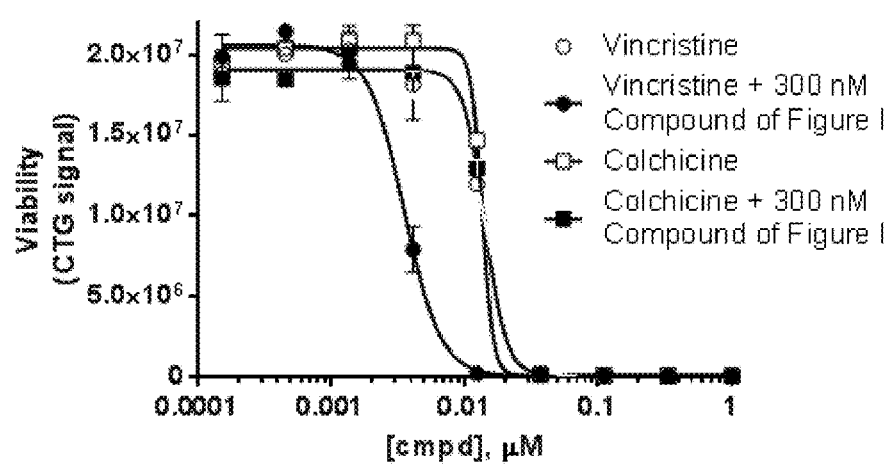
FIG. 3B summarizes the effect of the combination of the compound of Formula I and vincristine versus the combination of the compound of Formula I and colchicine in the DHL-10 cell line.
Figure 3C:
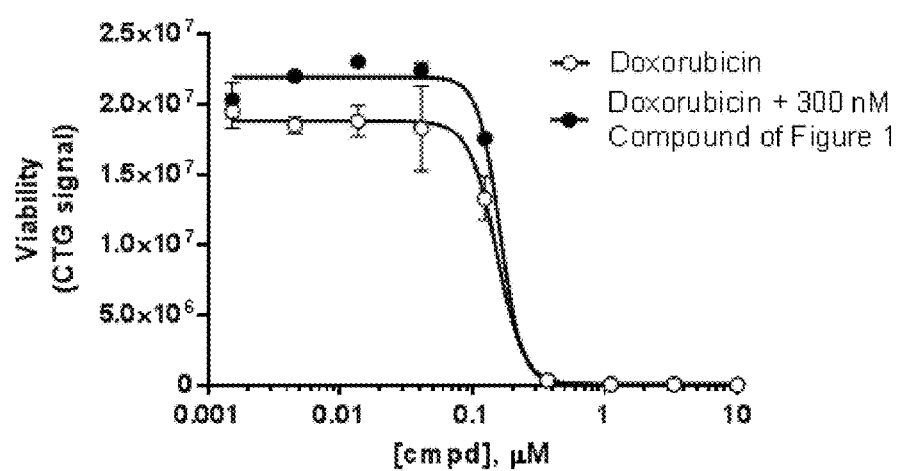
FIG. 3C summarizes the effect doxorubicin versus the combination of the compound of Formula I and doxorubicin in the DHL-10 cell line.

FIGS. 3A to 3C summarize the effect of the combination of the compound of Formula I and vincristine versus the combination of the compound of Formula I and combretastatin A4, the compound of Formula I and colchicine, the compound of Formula I and doxorubicin and the compound of formula I and taxol.

TABLE 2

| | Inhibition of cell viability $EC_{50}$ (nM) | | |
|---|---|---|---|
| Compound | No Compound of Formula I | +300 nM Compound of Formula I | Fold shift |
| Vincristine | 14.1 | 3.5 | 4.0 |
| Colchicine | 13.5 | 14.2 | 1.0 |
| Combretastatin A4 | 5.9 | 4.8 | 1.2 |
| Doxorubicin | 152 | 161 | 0.9 |
| Taxol | 7.1 | 5.6 | 1.3 |

Example 4

Comparison Effect of the Combination of the Compound of Formula I with Vincristine Versus Effect of the Combination of the Compound of Formula I with Vinblastine in the Malignant DLBCL B-Cell Line, DHL-10

This Example evaluates the efficacy of the compound of Formula I, or a pharmaceutically acceptable salt thereof, in combination with vincristine to inhibit malignant B-cell viability in the malignant diffuse large B-cell lymphoma (DLBCL) cell line DHL-10. This Example also evaluates and compares the efficacy of the compound of Formula I, or a pharmaceutically acceptable salt thereof, in combination with vinblastine to inhibit malignant B-cell viability in the malignant diffuse large B-cell lymphoma (DLBCL) cell line DHL-10.

Cell Titer Glo Viability Assay:

Vincristine and vinblastine were tested alone at 3 nM, or in combination with 100 nM of the compound of Formula I. The compound of Formula I, vinblastine sulfate and vincristine sulfate were dissolved in DMSO to prepare stock solutions in separate 96 well plates at 1000× for each compound so the final starting assay concentrations tested would be 100 nM for the compound of Formula I and 3 nM for vinblastine and vincristine. Compound plates were diluted and mixed together sequentially by 1:100 in RPMI without serum or additives creating a 10× stock in 2% DMSO of combinations or single agents. DHL-10 cells were seeded into a 96-well plate at 10,000 cells per well in 100 µl of in RPMI+10% FBS supplemented with 100 U/L penicillin-streptomycin. To each well containing cells, 11 µl of 10× compound mixture in serum-free media was added in a final concentration of 0.2% DMSO and cells were incubated at 37° C. in 5% $CO_2$ for 72 hours. Cell viability was assessed using Cell Titer Glo (CTG, Promega, Madison, Wis.) following the manufacturer's protocol and read on an Envision plate reader (Perkin Elmer, Waltham, Mass.). CTG signals were recorded for individual compound treatment and combinations. Results are shown in FIG. 4.

Figure 4:
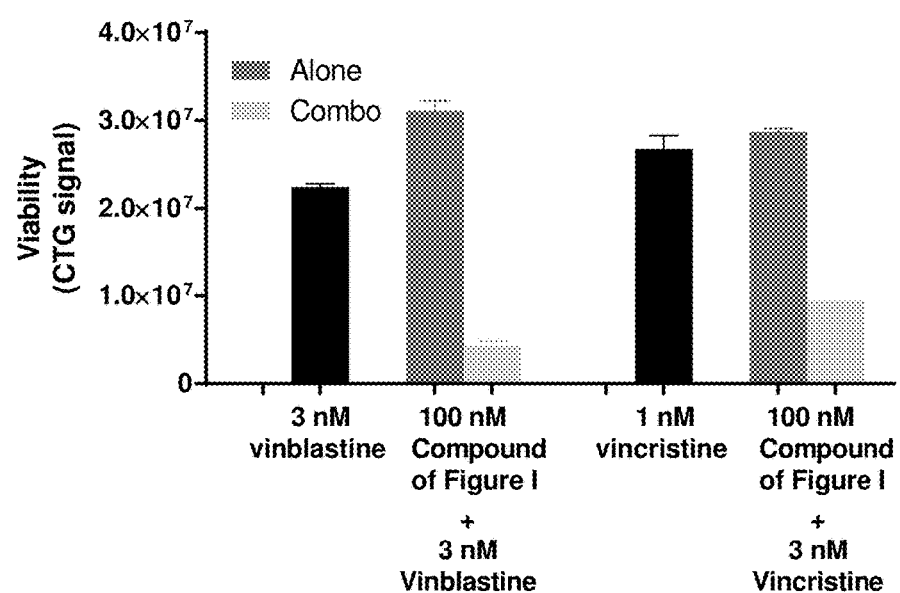
FIG. 4 depicts and summarizes the inhibitory effects of the combination of a compound of FIG. 1 and one of two of the vinca-alkaloids, vincristine and vinblastine respectively, in the DLBCL cell line, DHL-10 when compounds were co-administered.

FIG. 4 depicts and summarizes the inhibitory effects of the combination of the compound of FIG. 1 (the compound of Formula I) and one of two of the vinca alkaloids, vincristine and vinblastine respectively, in the DLBCL cell line, DHL-10 when compounds were co-administered (FIG. 4).

Example 5

Comparison Effect of the Compound of Formula I in Combination with Vincristine in a Syk-Expressing Solid Tumor Cell Line Versus Effect of the Compound of Formula I in Combination with Vincristine in a Non Syk-Expressing Solid Tumor Cell Line This Example evaluates the efficacy of the compound of Formula I, or a pharmaceutically acceptable salt thereof, in combination with vincristine to inhibit cell viability in the Syk-expressing pancreatic cell line, MIA PaCa-2. This Example also evaluates the efficacy of the combination of the compound of Formula I and vincristine to inhibit cell viability in the non-Syk expressing cell line, HepG2.

Cell Titer Glo Viability Assay:

Vincristine was tested alone, or in combination with 4 concentrations of the compound of Formula I (300, 100, 33, and 11 nM), in the malignant pancreatic cell line, MIA PaCa-2 and in the hepatocellular carcinoma HepG2 cell line. The compound of Formula I and vincristine sulfate were dissolved in DMSO to prepare stock solutions in separate 96 well plates at 1000× for each compound so the final starting assay concentrations tested would be 300-11 nM for the compound of Formula I and 3 nM for vincristine. Compound plates were diluted and mixed together sequentially by 1:100 in RPMI without serum or additives creating a 10× stock in 2% DMSO of combinations or single agents. MIA PaCa-2 and HepG2 cells were seeded into 96-well plates at 5,000 cells per well in 100 µl of in RPMI+10% FBS supplemented with 100 U/L penicillin-streptomycin. To each well containing cells, 11 µl of 10× compound mixture in serum-free media was added in a final concentration of 0.2% DMSO and cells were incubated at 37° C. in 5% $CO_2$ for 72 hours. Cell viability was assessed using Cell Titer Glo (CTG, Promega, Madison, Wis.) following the manufacturer's protocol on an Envision plate reader (Perkin Elmer, Waltham, Mass.). CTG signals were recorded for individual compound treatment and combinations. Results are shown in FIGS. 5A and 5B.

Figure 5A:
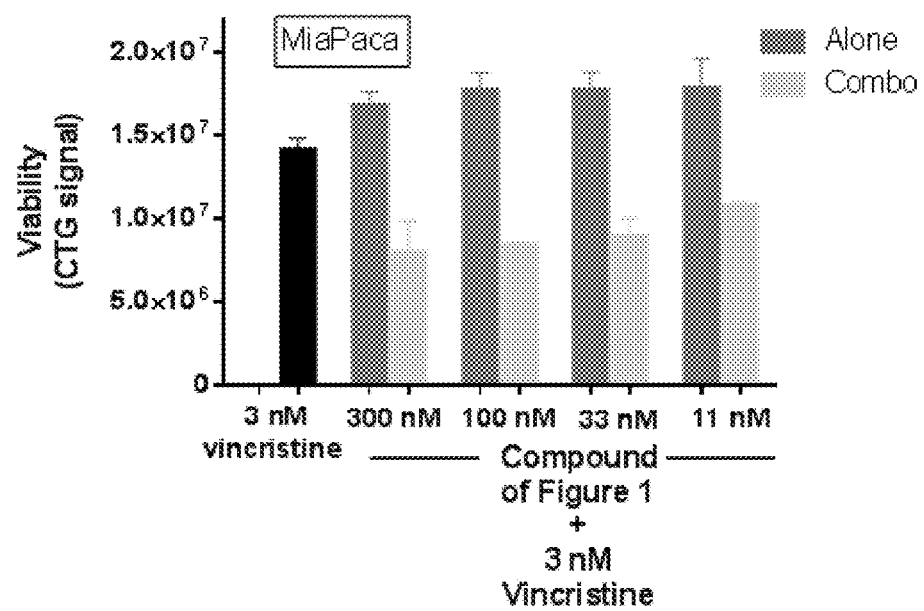
FIG. 5A summarizes the inhibition of cell viability by the combination of a compound of FIG. 1 and vincristine in the Syk-expressing malignant pancreatic cell line, MiaPaca.
Figure 5B:
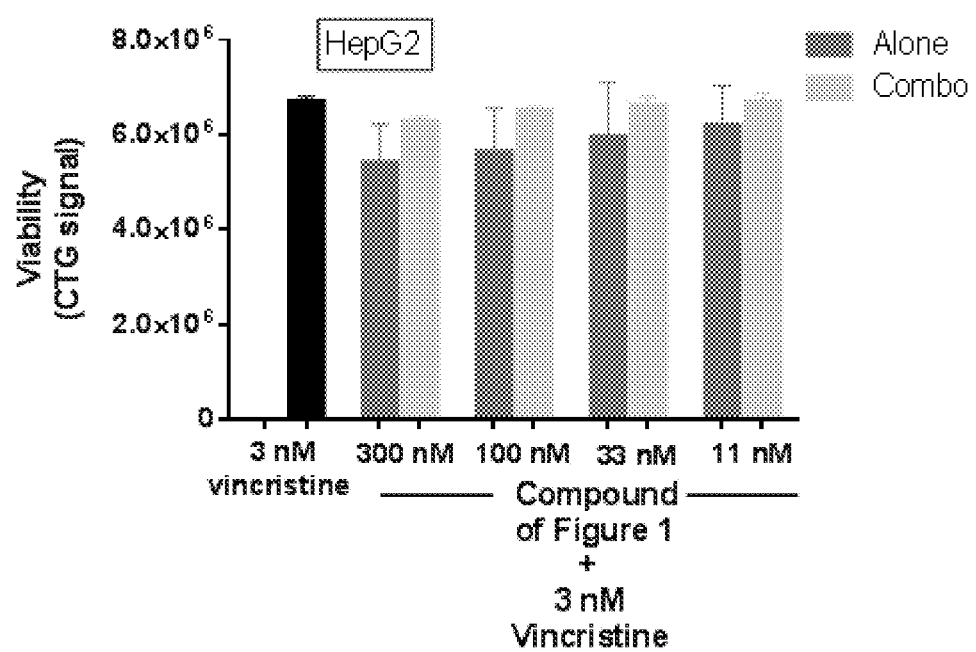
FIG. 5B summarizes the inhibition of cell viability by the combination of a compound of FIG. 1 and vincristine in the non-Syk expressing malignant colon cell line, HepG2.

FIGS. 5A and 5B summarize the inhibition of cell viability by the combination of the compound of Formula I and vincristine in the Syk-expressing malignant pancreatic cell line, MiaPaca (FIG. 5A) and in the non-Syk expressing malignant colon cell line, HepG2 (FIG. 5B).

Syk Protein Assay:

Cell lines were grown logarithmically overnight in RPMI supplemented with 10% FBS and 100 U/L penicillin-streptomycin. $1 \times 10^7$ were collected by centrifugation at 300×g at room temperature for 8 minutes in 50 mL tubes. Cell pellets were lysed on ice for 15 minutes in 200 uL of 1×RIPA buffer (Cell Signaling Technology, Danvers Mass.) containing protease (Roche, Palo Alto Calif.) and phosphatase inhibitors (Sigma, Saint Louis Mo.; Santa Cruz Technologies, Dallas Tex.). Cells lysates were transferred to 96-well V-bottom plates and used directly or frozen at −80° C. for use the next day. Proteins were separated with 4-12% SDS-Bis/Tris gels and blotted onto nitrocellulose. Blots were blocked in Rockland Odyssey blocking buffer and incubated with a total Syk antibody, 4D10 (Santa Cruz) and pSyk-$Y_{525/6}$ (Cell Signaling Technologies). The primary antibodies were diluted 1:1000 and incubated for 1 hour at room temperature. Blots were washed 3 times 5 minutes in Tris-buffered saline containing 1.0% Tween (TBS-T). Blots were then incubated goat αmouse IgG (H+L), AlexaFluor 680 (Life Sciences, Inc) and Goat αRabbit IgG (H+L), DyLight 800 (Thermo Scientific), each diluted 1:20,000 in blocking buffer, for 1 hour at room temperature. Blots were washed 3 times 5 minutes in TBS-T and analyzed on an Odyssey gel imager (LI-COR).

Figure 6:
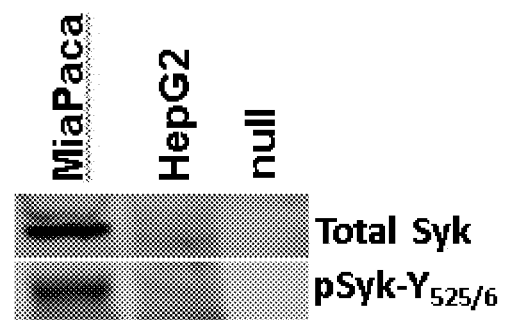
FIG. 6 depicts the level of Syk expression in the MiaPaca and HepG2 malignant colon cell lines.

FIG. 6 depicts the level of Syk expression in the MiaPaca and HepG2 malignant colon cell lines (FIG. 6).

Example 6

Figure 7:
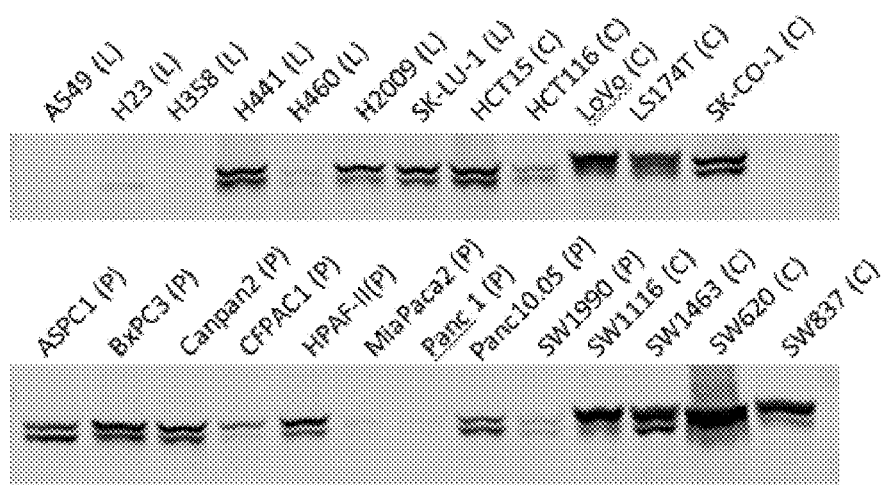
FIG. 7 summarizes the levels of Syk expression in malignant cell lines from lung, pancreas, and colon.

Determination of Syk Expression in Certain Malignant Solid Tumor Cell Lines (FIG. 7)

Syk Protein Assay:

Cell lines were grown logarithmically in overnight and $1 \times 10^7$ cells were collected by centrifugation at 300×g at room temperature for 8 minutes in 50 mL tubes. Cell pellets were lysed on ice for 15 minutes in 200 uL of 1×RIPA buffer (Cell Signaling Technology, Danvers Mass.) containing protease (Roche, Palo Alto Calif.) and phosphatase inhibitors (Sigma, Saint Louis Mo.; Santa Cruz Technologies, Dallas Tex.). Cells lysates were transferred to 96-well V-bottom plates and used directly or frozen at −80° C. for use the next day. Proteins were separated with 4-12% SDS-Bis/Tris gels and blotted onto nitrocellulose. Blots were blocked in Rockland Odyssey blocking buffer and incubated with a total Syk antibody, 4D10 (Santa Cruz). The primary antibody was diluted 1:1000 and incubated for 1 hour at room temperature. Blots were washed 3 times 5 minutes in Tris-buffered saline containing 1.0% Tween (TBS-T). Blots were then incubated goat αmouse IgG (H+L), AlexaFluor 680 (Life Sciences, Inc), diluted 1:20,000 in blocking buffer, for 1 hour at room temperature. Blots were washed 3 times 5 minutes in TBS-T and analyzed on an Odyssey gel imager (LI-COR). See FIG. 7.

Example 7

Efficacy Evaluation of Entospletinib and Vincristine Individually and in Combination in the SU-DHL-10 Mouse Xenograft Model of Diffuse Large B Cell Lymphoma Entospletinib was evaluated for efficacy in vivo as a single agent and in combination with vincristine in a subcutaneous cell line tumor xenograft model in male SCID beige mice using the human diffuse large B-cell lymphoma cell line, SU-DHL-10 in a 2×2 dose level matrix of Entospletinib and vincristine.

Formulation—Entospletinib was formulated in a complete vehicle of 0.5% HPMC-0.2% Tween 80 (pH 3.5 50 mM acetate buffer, and the lower dose was prepared by direct dilution). The high dose formulation was mixed using a stir bar (and Polytroned briefly as needed to break up clumps of compound) to form a yellow solution (pH=1.8), which became an opaque suspension within 30 minutes. The dosing suspension was prepared fresh daily and stored at 4° C. protected from light between treatments.

The formulation for the highest dose group of vincristine was prepared by diluting the stock solution with 0.9% sterile saline, and the lower dose was prepared by direct dilution of that stock with saline. The high dose formulation had a pH value of 7.08. The dosing formulations were prepared just prior to each treatment.

Animals—

Male Harlan SCID beige mice (C.B-17/IcrHsd-Prkdc$^{scid}$Lyst$^{bg-J}$) were used in this study. They were 6-7 weeks old on Day 1 of the experiment and were fed irradiated Harlan 2918.15 Rodent Diet and water ad libitum. Animals were housed in static cages with Bed-O'Cobs™ bedding (The Andersons Lab Bedding Products) inside Biobubble® Clean Rooms that provide H.E.P.A filtered air into the bubble environment at 100 complete air changes per hour. All treatments, body weight determinations, and tumor measurements were carried out in the bubble environment. The environment was controlled to a temperature range of 70°±2° F. and a humidity range of 30-70%.

Cells—

SU-DHL-10 cells were obtained from Leibniz Institute DSMZ-German Collection of Microorganisms and Cell Cultures (DSMZ). They were grown in RPMI 1640 medium which was modified with 1% 100 mM Na pyruvate, 1% 1M HEPES buffer, 1% of a 45% glucose solution and supplemented with 10% non-heat-inactivated Fetal Bovine Serum (FBS) and 1% 100× Penicillin/Streptomycin/L-Glutamine (PSG). The growth environment was maintained in an incubator with a 5% $CO_2$ atmosphere at 37° C. The cells were centrifuged at 200 rcf for 8 minutes at 8° C., the supernatant aspirated, and the pellet re-suspended in cold Dulbecco's Phosphate Buffered Saline (DPBS) by pipetting. An aliquot of the homogeneous cell suspension was diluted with a trypan blue solution and counted using a Luna automated cell counter. The pre-implantation cell viability was 91%. The cell suspension was centrifuged at 200 rcf for 8 minutes at 8° C. The supernatant was aspirated and the cell pellet was re-suspended in cold 50% serum-free medium: 50% Matrigel® Matrix (Corning) to generate a final concentration of 2.5E+07 cells/ml. The cell suspension was maintained on wet ice during implantation. Following implantation, an aliquot of the remaining cells was diluted with a trypan blue solution and counted to determine the post-implantation cell viability (91%). Test animals were implanted subcutaneously, high in the axilla (just under the fore limb) on Day 0 with 5.0×10$^6$ cells in 0.2 ml of 50% serum-free medium: 50% Matrigel® Matrix using a 27-gauge needle and syringe.

All mice were sorted into study groups based on tumor burden (estimated from caliper measurements). Efficacy was evaluated by tumor volume/weight monitored during and after treatment. Tumor burden (mg) was measured three times weekly by using caliper measurements and converting to tumor mass by the formula for the volume of a prolate ellipsoid assuming unit density as:

$$\text{Tumor burden (mg)} = (L \times W^2)/2$$

where L and W are the respective orthogonal tumor length and width measurements (mm). The criteria used for a successful distribution in this study was a mean tumor burden for all groups within 10% of the overall mean tumor burden for the study population Treatment began on Day 16 at an overall mean tumor burden of 197 mm$^3$.

Group 1: Vehicle control (entospletinib) 0.5% HPMC in 0.2% Tween 80 in 50 mM acetate buffer, pH 3.5 was dosed orally every twelve hours for 19 days (Days 16-32), and vehicle control (vincristine) 0.9% saline was dosed intravenously every 7 days, beginning on the third day of oral dosing (Days 18, 25, and 32).

Group 2: Entospletinib was dosed orally at 75 mg/kg every twelve hours for 6.5 days (Days 16-22); then lowered to 50 mg/kg every twelve hours for 10.5 days (Days 22-32), in combination with saline intravenously every 7 days, beginning on the third day of oral dosing (Days 18, 25, and 32).

Group 3: Entospletinib was dosed orally at 25 mg/kg every twelve hours for 19 days (Days 16-32), in combination with saline intravenously every 7 days, beginning on the third day of oral dosing (Days 18, 25, and 32).

Group 4: Vehicle for Entospletinib was dosed orally every twelve hours for 19 days (Days 16-32), in combination with vincristine at 0.5 mg/kg intravenously every 7 days, beginning on the third day of oral dosing (Days 18, 25, and 32).

Group 5: Vehicle for Entospletinib was dosed orally every twelve hours for 19 days (Days 16-32), in combination with vincristine at 0.15 mg/kg intravenously every 7 days, beginning on the third day of oral dosing (Days 18, 25, and 32).

Group 6: Entospletinib was dosed orally at 75 mg/kg every twelve hours for 6.5 days (Days 16-22); then lowered due to body weight loss to 50 mg/kg every twelve hours for 10.5 days (Days 22-32), in combination with vincristine at 0.5 mg/kg intravenously every 7 days, beginning on the third day of oral dosing (Days 18, 25, and 32).

Group 7: Entospletinib was dosed orally at 25 mg/kg every twelve hours for 19 days (Days 16-32), in combination with vincristine at 0.5 mg/kg intravenously every 7 days, beginning on the third day of oral dosing (Days 18, 25, and 32).

Group 8: Entospletinib was dosed orally at 75 mg/kg every twelve hours for 6.5 days (Days 16-22); then lowered to 50 mg/kg every twelve hours for 10.5 days (Days 22-32), in combination with vincristine at 0.15 mg/kg intravenously every 7 days, beginning on the third day of oral dosing (Days 18, 25, and 32).

Group 9: Entospletinib was dosed orally at 25 mg/kg every twelve hours for 19 days (Days 16-32), in combination with vincristine at 0.15 mg/kg intravenously every 7 days, beginning on the third day of oral dosing (Days 18, 25, and 32).

All mice were dosed according to individual body weight on the day of treatment (0.1 ml/20 g).

On the 16$^{th}$ day post-tumor implantation, animals with established tumors (n=9 animals per group) were treated for 3 days by oral gavage with either vehicle or Entospletinib at 75 mg/kg or 25 mg/kg twice daily (BID). On the third day, the animals received an intravenous dose of saline or vincristine and plasma and tumor samples were collected 0.5, 2 or 12 hours post dose. An additional 12 animals per group were treated for 19 days (starting on Day 16 of study) by oral gavage with either vehicle or Entospletinib at the planned dose levels of 25 mg/kg and 75 mg/kg BID and intravenous administration of either saline or vincristine (0.5 mg/kg and 0.15 mg/kg every 7 days (Q7D) for 3 doses starting on the third day after the start of Entospletinib (Day 19 of study). The 75 mg/kg BID dose level of Entospletinib was administered for 6.5 days and then reduced to 50 mg/kg BID due to the higher than planned plasma concentrations measured in plasma samples collected on the third day of dosing, and weight loss in group being co-treated with 0.5 mg/kg vincristine. This dose level is designated 75/50 mg/kg.

Efficacy was evaluated by tumor volume measurements. Plasma levels of Entospletinib and vincristine were evaluated on the third day of dosing Entospletinib (Day 19) and the last day of dosing (Day 32). Tolerability was evaluated by daily observations, body weight (3 times per week) and circulating blood cell counts at the end of the study.

All dose levels and combinations evaluated were tolerated, following the 75 mg/kg entospletinib dose reduction to 50 mg/kg. The doses of 25 and 50 mg/kg BID Entospletinib resulted in plasma concentrations at the end of study that exceed the in vitro pervanadate-stimulated mouse whole blood $EC_{50}$ and $EC_{50}$ values for inhibition of SYK, respectively, at $C_{min}$ (trough). Vincristine administered at both 0.15 and 0.5 mg/kg resulted in significant inhibition of tumor growth. Entospletinib dosed alone at 25 or 75/50 mg/kg inhibited tumor growth but to a lesser degree than that seen with vincristine.

The addition of Entospletinib at the 75/50 mg/kg level resulted in significant improvement in tumor growth inhibition over vincristine alone with an increase in % tumor growth inhibition (TGI) from 85% to 96% for 0.5 mg/kg vincristine and an increase in % TGI form 42% to 71% for 0.15 mg/kg vincristine. The addition of 25 mg/kg Entospletinib to either dose of vincristine did not significantly increase the tumor growth inhibition. While the groups receiving either Entospletinib or vincristine as single agents had no complete or partial regressions, 50% of the mice receiving the combination of 75/50 mg/kg Entospletinib with 0.5 mg/kg vincristine had partial responses and 8% had complete regression and 8% were tumor free at the end of study. The tumor growth inhibition and tolerability of Entospletinib and vincristine alone and in combination are summarized in the table below.

Summary of Efficacy with Entospletinib and Vincristine at Tolerated Doses

| Treatment (Group number) | Day 31% Tumor Growth Inhibition[a] | Significance (P value) |
| --- | --- | --- |
| Vehicle for ENTO BID + Vehicle for VCR Q7Dx3 (1) | NA[b] | |
| ENTO 75/50 mg/kg BID + Vehicle for VCR Q7Dx3 (2) | 39 | <0.00001 vs. vehicle |
| ENTO 25 mg/kg BID + Vehicle for VCR Q7Dx3 (3) | 20 | 0.0455 vs. vehicle |
| Vehicle for ENTO + VCR 0.5 mg/kg Q7Dx3 (4) | 85 | <0.00001 vs. vehicle |
| Vehicle for ENTO + VCR 0.15 mg/kg Q7Dx3 (5) | 42 | <0.00001 vs. vehicle |
| ENTO 75/50 mg/kg BID + VCR 0.5 mg/kg Q7Dx3 (6) | 96 | 0.001 vs. VCR 0.5 mg/kg |
| ENTO 25 mg/kg BID + VCR 0.5 mg/kg Q7Dx3 (7) | 90 | 0.3866 vs. VCR 0.5 mg/kg |
| ENTO 75/50 mg/kg BID + VCR 0.15 mg/kg Q7Dx3 (8) | 71 | <0.00001 vs. VCR 0.15 mg/kg |
| ENTO 25 mg/kg BID + VCR 0.15 mg/kg Q7Dx3 (9) | 58 | 0.0754 vs. VCR 0.15 mg/kg |

[a]The percentage of tumor growth inhibition (% TGI) was calculated using the delta of the mean treated tumor values divided by the delta of the mean control tumor values expressed as a percentage and then subtracted from 100%.
[b]NA does not apply since this is the control The administration of combinations of Entospletinib with vincristine to animals baring the SU-DHL-10 subcutaneous xenograft demonstrated that a dose of entospletinib which results in a calculated $EC_{50}$ trough coverage of SYK resulted in significant increase in tumor growth inhibition as well as an increase to 50% partial tumor regressions compared to 0% with entospletinib or vincristine treatment alone, with 8% complete regression.

What is claimed is:

1. A method for treating cancer in a human in need thereof, comprising administering to the human a therapeutically effective amount of a compound of formula (I):

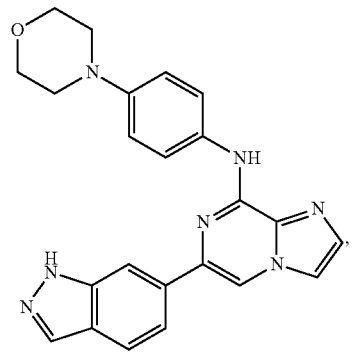

or a pharmaceutically acceptable salt thereof, and a therapeutically effective amount of a vinca alkaloid, or a pharmaceutically acceptable salt, wherein the cancer expresses spleen tyrosine kinase (Syk) activity and is selected from the group consisting of pancreatic cancer, lung cancer, colorectal cancer, ovarian cancer, breast cancer, esophageal cancer, adenocarcinoma and hepatocellular cancer.

2. The method of claim 1, wherein the vinca alkaloid is selected from the group consisting of vincristine, vinblastine, vindesine, vinorelbine, desoxyvincaminol, vincaminol, vinburnine, vincamajine, and vineridine.

3. The method of claim 2, wherein the vinca alkaloid is selected from the group consisting of vincristine, vinblastine, vindesine, and vinorelbine.

4. The method of claim 1, wherein the vinca alkaloid is vincristine.

5. The method of claim 1, wherein the vinca alkaloid is vinblastine.

6. The method of claim 1, wherein the compound of formula (I) is present in a pharmaceutical composition comprising the compound of formula (I), and at least one pharmaceutically acceptable excipient.

7. The method of claim 1, wherein the compound of formula (I) or a pharmaceutically acceptable salt thereof is administered before the vinca alkaloid, or a pharmaceutically acceptable salt thereof.

8. The method of claim 1, wherein the vinca alkaloid, or a pharmaceutically acceptable salt thereof, is administered before the compound of formula (I) or a pharmaceutically acceptable salt thereof.

9. The method of claim 1, wherein the compound of formula (I) or a pharmaceutically acceptable salt thereof, and the vinca alkaloid, or a pharmaceutically acceptable salt thereof, are administered simultaneously.

10. The method of claim 1, wherein each of the compound of formula (I) and the vinca alkaloid, or pharmaceutically acceptable salts thereof, is independently administered, wherein the compound of formula (I) is administered twice a day and wherein further the vinca alkaloid is administered once a week.

11. The method of claim 1, wherein the compound of formula (I) or a pharmaceutically acceptable salt thereof is administered at a dose between 100 mg and 800 mg and the vinca alkaloid, or a pharmaceutically acceptable salt thereof, is administered at a dose between about 0.1 mg-$M^2$ and 1.5 mg-$M^2$.

12. The method of claim 1, wherein the compound of formula (I) or a pharmaceutically acceptable salt thereof is administered at a dose between 200 mg and 400 mg and the vinca alkaloid or a pharmaceutically acceptable salt thereof is administered at a dose between 0.25 mg-M$^2$ and 1.0 mg-M$^2$, wherein the vinca alkaloid is selected from the group consisting of vincristine and vinblastine.

13. The method of claim 1, wherein the human who has cancer is (i) refractory to at least one chemotherapy treatment, or (ii) is in relapse after treatment with chemotherapy, or a combination thereof.

14. The method of claim 1, wherein the human has not previously been treated for the cancer.

15. The method of claim 1, wherein the human has a 17p deletion, a TP53 mutation, or a combination thereof.

16. The method of claim 15, wherein the human further has NOTCH1, a SF3B1 mutation, a 11q deletion, or any combination thereof.

17. The method of claim 1, wherein:
the vinca alkaloid is selected from the group consisting of vincristine and vinblastine, and
the human is (i) refractory to at least one anti-cancer treatment, or (ii) in relapse after treatment with at least one anti-cancer therapy, or a combination thereof.

18. The method of claim 17 wherein the human is not undergoing any other anti-cancer treatments.

19. The method of claim 17, wherein the human is not undergoing any other anti-cancer treatments using one or more PI3K inhibitors.

20. The method of claim 18, wherein the human is refractory to at least one anti-cancer treatment.

21. The method of claim 18, wherein the human is in relapse after treatment with at least one anti-cancer treatment.

22. The method of claim 18, wherein about 200 mg to about 800 mg of the compound of formula (I), or a pharmaceutically acceptable salt thereof, is administered to the human twice daily.

23. The method of claim 22, wherein 100-400 mg of the compound of formula (I), or a pharmaceutically acceptable salt thereof, is administered to the human twice daily.

24. The method of claim 18, wherein the human has a 17p deletion, a TP53 mutation, or a combination thereof and about 400 mg of the compound of formula (I), or a pharmaceutically acceptable salt thereof, is administered to the human twice daily.

25. The method of claim 1, wherein the cancer is pancreatic cancer.

26. The method of claim 1, wherein each of the compound of formula (I) and the vinca alkaloid, or pharmaceutically acceptable salts thereof, is independently administered, wherein the compound of formula (I) is administered once.

27. The method of claim 1, wherein each of the compound of formula (I) and the vinca alkaloid, or pharmaceutically acceptable salts thereof, is independently administered, wherein the compound of formula (I) is administered once a day and wherein further the vinca alkaloid is administered once a week.

28. The method of claim 1, wherein the cancer is lung cancer.

29. The method of claim 1, wherein the cancer is colorectal cancer.

30. The method of claim 1, wherein the cancer is ovarian cancer.

31. The method of claim 1, wherein the cancer is breast cancer.

32. The method of claim 1, wherein the cancer is esophageal cancer.

33. The method of claim 1, wherein the cancer is adenocarcinoma.

34. The method of claim 1, wherein the cancer is hepatocellular cancer.

* * * * *